(12) United States Patent
Heinz

(10) Patent No.: US 8,308,472 B2
(45) Date of Patent: Nov. 13, 2012

(54) DEVICE FOR THE PRODUCTION AND/OR HANDLING OF A HIGHLY PURE OBJECT

(75) Inventor: Jochen Heinz, Kiel (DE)

(73) Assignee: Transcoject GmbH & Co. KG, Neumuenster (DE)

( * ) Notice: Subject to any disclaimer, the term of this patent is extended or adjusted under 35 U.S.C. 154(b) by 0 days.

(21) Appl. No.: 12/501,154

(22) Filed: Jul. 10, 2009

(65) Prior Publication Data

US 2010/0009022 A1 Jan. 14, 2010

Related U.S. Application Data

(60) Division of application No. 11/209,312, filed on Aug. 23, 2005, now Pat. No. 7,584,591, which is a continuation-in-part of application No. 10/717,209, filed on Nov. 19, 2003, now abandoned, and a continuation-in-part of application No. 11/134,692, filed on May 20, 2005, now abandoned, which is a continuation-in-part of application No. 10/717,209, filed on Nov. 19, 2003, now abandoned, and a continuation-in-part of application No. PCT/DE03/03861, filed on Nov. 21, 2003.

(30) Foreign Application Priority Data

Nov. 22, 2002 (DE) .................................. 102 54 762

(51) Int. Cl.
*B29C 45/42* (2006.01)
*B29C 45/43* (2006.01)
(52) U.S. Cl. .................. 425/444; 425/437; 425/556
(58) Field of Classification Search ............... 425/436 R, 425/436 RM, 437, 444, 556, DIG. 102
See application file for complete search history.

(56) References Cited

U.S. PATENT DOCUMENTS

| 2,400,722 | A |   | 5/1946  | Swan |
|-----------|---|---|---------|------|
| 3,128,499 | A |   | 4/1964  | Smolenski |
| 3,375,309 | A | * | 3/1968  | Stevens .......................... 264/121 |
| 3,539,216 | A | * | 11/1970 | Forcier .......................... 294/64.3 |
| 3,789,093 | A |   | 1/1974  | Bose |
| 3,937,609 | A |   | 2/1976  | Ryder |
| 3,963,404 | A | * | 6/1976  | Pollock et al. ................ 425/150 |

(Continued)

FOREIGN PATENT DOCUMENTS

DD 262 182 11/1988

(Continued)

*Primary Examiner* — Yogendra Gupta
*Assistant Examiner* — Emmanuel S Luk
(74) *Attorney, Agent, or Firm* — Cozen O'Connor

(57) ABSTRACT

A method of manufacturing or handling a substantially pure object includes shielding the substantially pure object from the environment by substantially enveloping the object in a fluid. A system for manufacturing a substantially pure object includes a mold for forming the object, and a machine adapted to remove the object from the mold. The machine includes a handling device for gripping the object and removing it from the mold. The handling device includes at least one nozzle through which fluid is delivered to substantially envelope the object during, for example, removal of the object from the mold. The object may be a medical object, such as a syringe, or a component or part thereof, such as a syringe barrel or plunger. In a preferred aspect, a molding process is conducted in a room exhibiting less than Class 100 conditions and/or in such a way that the object does not need to be subsequently cleaned or rinsed, as by air or water washing.

12 Claims, 21 Drawing Sheets

U.S. PATENT DOCUMENTS

| | | | | |
|---|---|---|---|---|
| 4,029,351 A | * | 6/1977 | Apgar et al. | 294/64.3 |
| 4,037,830 A | | 7/1977 | Poluzzi et al. | |
| 4,151,236 A | | 4/1979 | Ryder | |
| 4,176,153 A | | 11/1979 | Weiler et al. | |
| 4,422,998 A | | 12/1983 | Sorensen | |
| 4,534,921 A | | 8/1985 | Fierkens et al. | |
| 4,596,110 A | | 6/1986 | Weiler | |
| 4,703,781 A | | 11/1987 | Meyer et al. | |
| 4,707,966 A | | 11/1987 | Weiler et al. | |
| 4,718,463 A | | 1/1988 | Jurgens, Jr. et al. | |
| 4,723,480 A | | 2/1988 | Yagi et al. | |
| 4,770,680 A | | 9/1988 | Machida et al. | |
| 4,976,900 A | | 12/1990 | Tsutsumi | |
| 5,015,425 A | | 5/1991 | Mimata et al. | |
| 5,067,762 A | * | 11/1991 | Akashi | 294/64.3 |
| 5,080,549 A | * | 1/1992 | Goodwin et al. | 414/744.8 |
| 5,141,430 A | | 8/1992 | Maus et al. | |
| 5,169,418 A | | 12/1992 | Honda et al. | |
| 5,316,560 A | | 5/1994 | Krone-Schmidt et al. | |
| 5,324,155 A | * | 6/1994 | Goodwin et al. | 414/744.5 |
| 5,620,425 A | | 4/1997 | Heffernan et al. | |
| 5,687,542 A | | 11/1997 | Lawecki et al. | |
| 5,803,979 A | * | 9/1998 | Hine et al. | 134/2 |
| 5,901,865 A | | 5/1999 | Weiler et al. | |
| 5,935,511 A | * | 8/1999 | Brown | 264/551 |
| 5,948,341 A | * | 9/1999 | Diamond et al. | 264/335 |
| 5,979,475 A | * | 11/1999 | Satoh et al. | 134/140 |
| 6,010,400 A | | 1/2000 | Krainiak et al. | |
| 6,065,270 A | | 5/2000 | Reinhard et al. | |
| 6,099,056 A | * | 8/2000 | Siniaguine et al. | 294/64.3 |
| 6,145,277 A | | 11/2000 | Lawecki et al. | |
| 6,164,044 A | | 12/2000 | Porfano et al. | |
| 6,168,697 B1 | * | 1/2001 | Siniaguine et al. | 204/298.15 |
| 6,189,195 B1 | | 2/2001 | Reilly et al. | |
| 6,189,292 B1 | | 2/2001 | Odell et al. | |
| 6,250,052 B1 | | 6/2001 | Porfano et al. | |
| 6,263,641 B1 | | 7/2001 | Odell et al. | |
| 6,322,116 B1 | * | 11/2001 | Stevens | 294/64.3 |
| 6,386,850 B1 | * | 5/2002 | Salerno et al. | 425/112 |
| 6,398,031 B1 | | 6/2002 | Frezza | |
| 6,635,216 B2 | | 10/2003 | Dundas | |
| 6,887,418 B2 | | 5/2005 | Olaru | |
| 7,261,549 B2 | * | 8/2007 | Wennberg | 425/444 |
| 7,510,226 B2 | * | 3/2009 | Akiyama | 294/64.3 |
| 7,514,031 B2 | * | 4/2009 | Howlett | 264/334 |
| 2002/0090415 A1 | | 7/2002 | Herbst | |

FOREIGN PATENT DOCUMENTS

| | | |
|---|---|---|
| DE | 27 37 397 | 3/1978 |
| DE | 198 01 977 | 7/1999 |
| DE | 100 29 154 | 1/2002 |
| DE | 100 50 660 | 4/2002 |
| DE | 101 44 409 | 3/2003 |
| EP | 0 246 587 | 11/1987 |
| EP | 0 849 173 | 6/1998 |

* cited by examiner

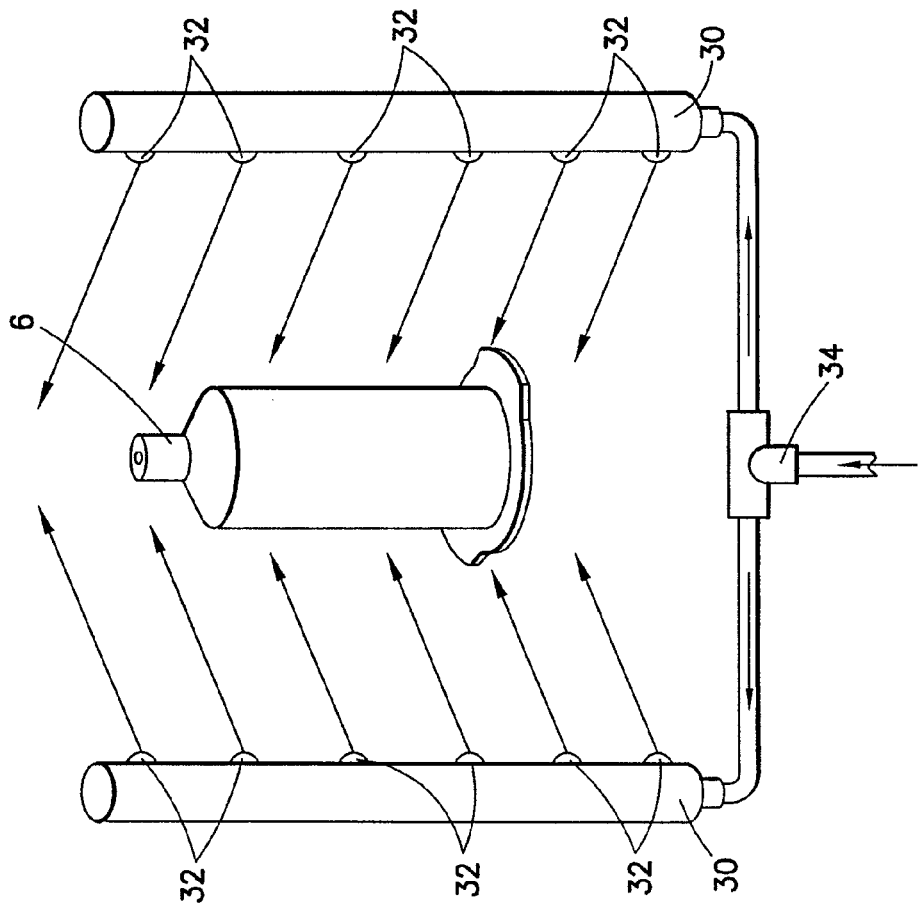
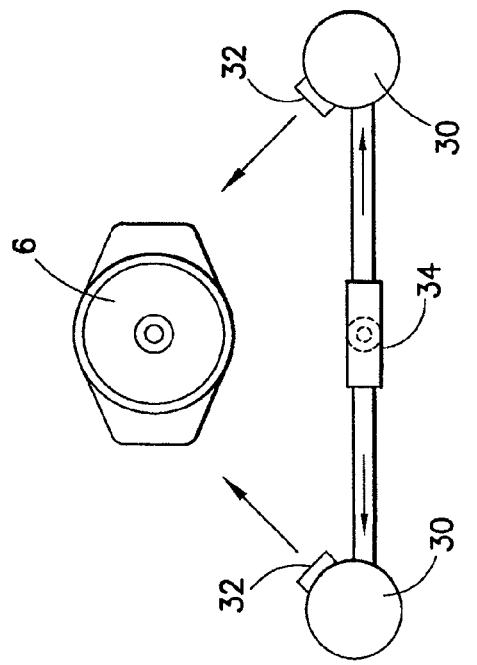

BARREL PROCESS

TIP CAP PROCESS

CARRIER PROCESS

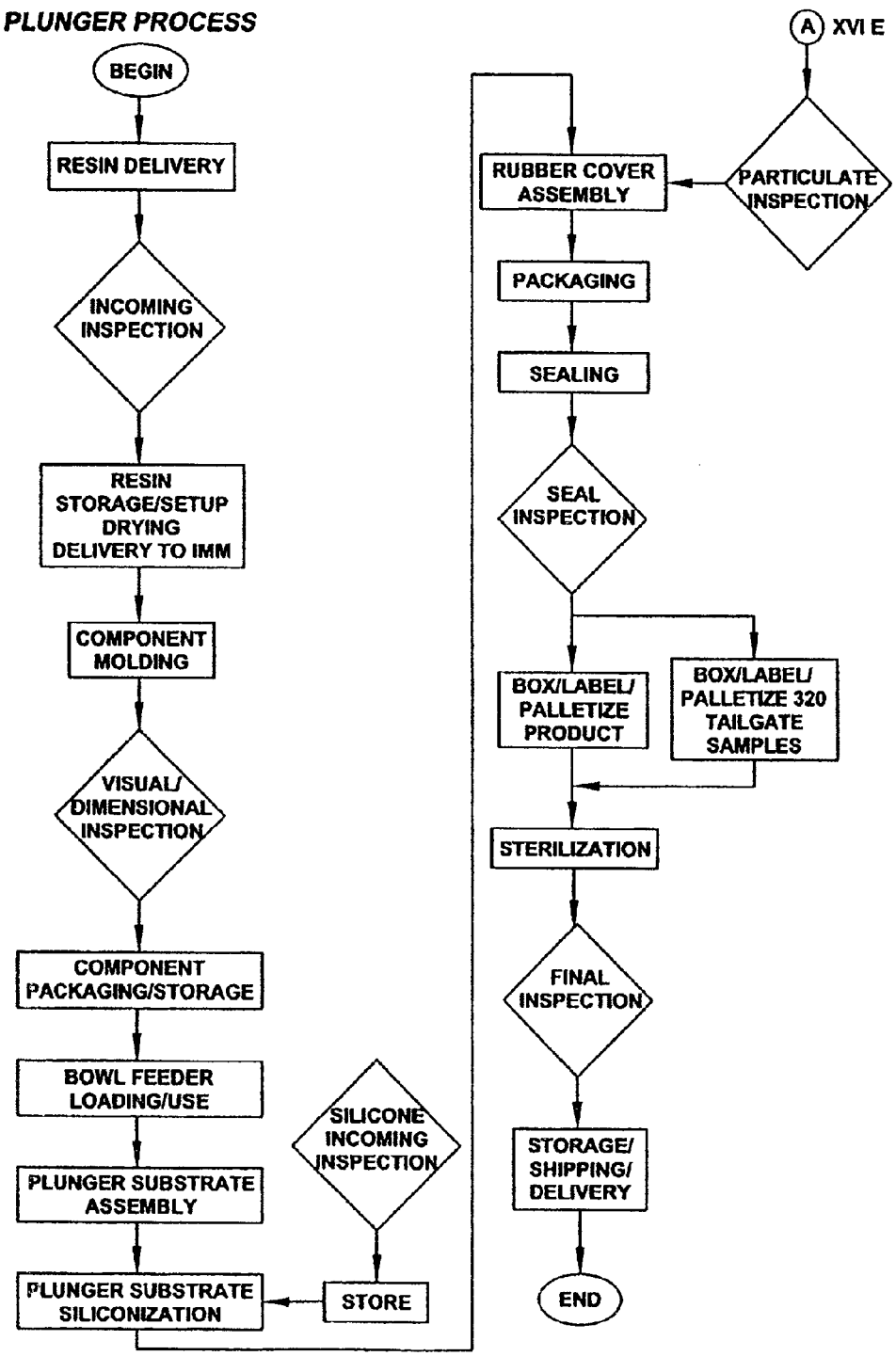

RUBBER COVER PROCESS

DEVICE FOR THE PRODUCTION AND/OR HANDLING OF A HIGHLY PURE OBJECT

CROSS REFERENCE TO RELATED APPLICATIONS

This application is a divisional of U.S. application Ser. No. 11/209,312, which was filed with the U.S. Patent and Trademark Office on Aug. 23, 2005, and which is a continuation-in-part of U.S. application Ser. No. 10/717,209 filed on Nov. 19, 2003, claiming priority from German Application No. 102 54 762.9 filed on Nov. 22, 2002. U.S. application Ser. Nos. 11/209,312 and 10/717,209 are incorporated in their entireties herein by reference.

U.S. application Ser. No. 11/209,312 is also a continuation-in-part of U.S. application Ser. No. 11/134,692 filed on May 20, 2005, now abandoned, claiming priority from PCT/DE2003/003861 filed on Nov. 21, 2003 and claiming priority under 35 U.S.C. §119(a) and 35 U.S.C. §365(b) from German Application No. 102 54 762.9. U.S. application Ser. No. 11/134,692 is incorporated in its entirety herein by reference.

BACKGROUND OF THE INVENTION

1. Field of the Invention

The invention concerns a procedure for the manufacture and/or handling of a substantially pure object, in particular a medical container, for example, a prefillable container for the reception of drugs. Furthermore, the invention concerns a corresponding device for the handling of such a substantially pure object.

2. Description of the Related Art

There are medical containers known, which are used for the storing of medicinal and pharmaceutical substances. In particular, such containers are prefillable containers such as, for example, prefillable bottles or prefillable syringes made from glass or plastic, which are delivered, prefilled with a drug.

These types of container for the storage of medicaments and pharmaceutics have to essentially satisfy two aspects, namely to protect the substance to be stored from changes and to also keep the contents of the container free from impurities. The official minimum requirements for this are, for example, described in the Pharmacopoeia and consequently conclusively stipulated. In detail, the demands on products may go far beyond these.

Potential impurities such as particles or microbes may not only get into the container from the environment, but more often than not they may also originate from the container itself, that is to say, for example, either during or through the molding or production process of the container. As a result the relevant regulations stipulate the highest values for permissible particulate and endotoxin loads.

In particular, contamination of a plastic article may occur when following the manufacturing and ejection process, the plastic article exhibits an electrostatic charge, which attracts particles from the environment and prevents the attached particles from being rinsed off. Therefore, in the customary manufacturing process a procedure is used in order to discharge the plastic parts after ejection. At the same time, however, the discharging is often incomplete and recharging effects occur, through which charges from the inside of the plastic parts reach the surfaces over a longer period of time.

Usually particulate and endotoxin loads are prevented through the washing of the container after molding and before filling, as is described in U.S. Pat. No. 4,718,463. What is more, pyrogens are generally removed from these containers through the application of high temperatures up to 3000 Celsius. This application of high temperatures may, however, only be used for glass containers since generally speaking, plastic containers would be destroyed at these temperatures.

Therefore, other procedures are used for the manufacture and cleaning of plastic containers. U.S. Pat. No. 5,620,425 describes the manufacture of a prefillable syringe cylinder in a Class 100 clean room, which ought to prevent impurities during the manufacture of the syringe body. However, the complete production of a syringe body or of a syringe in a clean room is only possible at great expense. A Class 100 clean room atmosphere is only possible with the creation of a laminar flow, which can only be maintained with a high level of difficulty, especially when personnel are working in the clean room and an injection molding machine, requiring the opening and closing of mold platens, is used. Therefore the conditions described in U.S. Pat. No. 5,620,425 during the manufacture of a plastic syringe in injection molding are not able to be maintained at all or only with great difficulty, in order to achieve the required sterility. In addition to this the clean room conditions and their suitability for the respective product first have to be validated regarding cost and then have to be intensively monitored during operation. Overall the running of this type of clean room thus presents a considerable expense, which leads to a considerable increase in the cost of the manufactured product.

Therefore, U.S. Pat. Nos. 6,164,044, 6,189,292, 6,263,641 and 6,250,052 describe a further manufacturing procedure for the manufacture of prefillable glass or plastic containers. In accordance with the procedures described in these patents, the containers or the syringe cylinders are put into a closed system following their production by the pouring or forming of the glass or the injection molding of the plastics for further processing. This system consists of individual containers or cabinets in which a clean room atmosphere prevails. When the containers manufactured outside of this clean room atmosphere are brought into the closed system they are first cleaned by a current of purified air so that any particles or germs potentially attached to the containers are rinsed off or sprayed away from the containers. The containers cleaned in this way are subsequently further processed in the system in which Class 100 clean room conditions prevail.

Even this arrangement has the disadvantage that Class 100 clean room conditions have to be achieved for all of the handling and for the filling into the closed cabinets or containers. Furthermore, there is the danger that microbes or particles are attached to the containers manufactured outside of the clean room system despite the initial cleaning.

Therefore, there is a need for a new system, device and method for manufacturing and/or handling a substantially pure object, such as a medical container, which allows for more cost effective and more simple production and which simultaneously is able to guarantee a greater purity. In particular, an efficient procedure for the manufacture of medical containers that satisfies and/or exceeds the requirements of the Pharmacopoeia with regard to cleanliness, in particular with regard to particles and/or endotoxins, is desirable. Further, a system, device or method that can avoid the expense and complexity of very sterile clean rooms, in particular those of Class 100, and the need for air or water washing of the container after molding, is particularly desirable.

SUMMARY OF THE INVENTION

The system, device and/or method of the present invention are directed, in a preferred embodiment, to the manufacture and/or handling of a substantially pure object. Such an object, for example, may be a medical object, such as a medical container or syringe, which has to be substantially pure, that is to say essentially or substantially free from microbes and particles.

The present invention, in a preferred embodiment, provides a method for molding a component of a medical container that is substantially pure, without the need for subsequent air or water washing and/or the strict conditions of Class 100 clean rooms.

According to a preferred embodiment of the procedure, the substantially pure object is protected from the environment during a handling process by a fluid that envelops or surrounds the object. In this way, those parts or components of an object that have to exhibit the required purity are enveloped by the flowing fluid during critical steps of the manufacturing and/or handling process, and are therefore maintained in a defined protective atmosphere. In this way, an initially substantially pure object is not contaminated through contact with the environment during handling and further processing. By providing a protected atmosphere for the object, a particular clean room and/or subsequent purification, cleaning or washing step is not required and the manufacturing process is simplified.

Furthermore, the present invention may provide a manufactured object of greater purity than with current techniques because contamination of the object can be prevented from the outset, instead of being removed again in later purification, cleaning or washing steps, when a complete removal of impurities during the cleaning process is, for the most part, not possible.

Moreover, compared with known procedures in which the object is rinsed with a fluid for a short time to clean or rinse contaminants therefrom, the present invention provides a protective atmosphere for an object to prevent contaminants from contacting or adhering thereto in the first place, thereby avoiding the need for air or water washing. In addition, the protective atmosphere may be provided at lower fluid flow rates and fluid quantities than is required for standard air or water washing techniques, which reduces the complexity and cost of the process.

Furthermore, the present invention eliminates production steps required in known manufacturing processes, which not only shortens the entire manufacturing procedure, increases its efficiency and reduces its costs, but also reduces the risk of the object being contaminated during the process. Through the direct protection of the object by the surrounding fluid during the manufacturing process and/or during handling, the transfer steps between different environments can be avoided. In a preferred embodiment, the object always remains in the environment generated by the circulating fluid. However, in steps subsequent to removal of the object from the molding machine, the object may be handled and/or processed in another environment, such as a Class 1000 or a Class 10,000 environment. Examples of steps subsequent to object removal may include, but are not limited to, siliconization, inspection and packaging steps.

Preferably, the object is a matter of a thermo-formed object in a mold where the object is protected from the environment during the entire removal process from the mold by the enveloping fluid. The object is, for example, an object made from metal or plastic, which has been manufactured in an injection process, for example, an injection molding or a die-casting in the mold. In a preferred embodiment, the invention exploits the effect that a thermo-formed object, for example, an object made from liquid plastic, exhibits perfect purity after it sets. This especially applies with regard to particles and, due to melting temperatures up to more than 300° Celsius, endotoxins.

By enveloping the freshly molded object during its removal from the mold, the object, which is pure because of the manufacturing process, is prevented from subsequently being contaminated. Due to the fluid envelope or the fluid sheathing, the object does not contact and is therefore not contaminated by the ambient air, which prevents the object from being contaminated from the outset. This has the advantage that no especially pure environmental conditions have to be achieved so, for example, the expensive and costly Class 100 clean rooms can be done away with during the manufacture of medical objects or containers. Because the present invention prevents object contamination from the outset, cleaning or rinsing of the object prior to further processing, as is required with current technology, is avoided. In compliance with a preferred embodiment of the present invention, the substantially pure object, which is protected from contamination by the enveloping fluid, may be passed on directly for further processing without an intermediate step. In this way, a very cost effective and efficient manufacturing process can be achieved.

The system, device and/or procedure of the present invention are preferably suitable for the manufacture of an object that is or is a component part of a medical container. This type of container may be, for example, a prefillable bottle or a prefillable syringe made from a suitable plastic, in particular a barrier plastic, which is formed in the mold. The forming of the container part or of the container is preferably done in an injection molding or an injection blow molding procedure. In compliance with a preferred aspect of the invention, all parts or components of a medical container, in particular those parts that contact a drug or pharmaceutical, may be manufactured and handled without becoming contaminated in connection with the molding process. At the same time, by using a fluid shield or environment during at least the molding step, the present invention preferably renders a subsequent fluid washing or cleaning step unnecessary. Preferably, the original purity or the sterility at the time of removal from the mold is maintained up until filling without the handling process having to be run in a special Class 100 clean room.

The fluid with which the object is enveloped may be a liquid or a gas. In a preferred embodiment, the fluid is a gas and, in particular, air or filtered air. The required freedom of the gas or of the air from microbes and particles can be guaranteed through proper filtration. Preferably, 0.2 µm filters or filters with even smaller pore diameters are used to guarantee the required purity of the air. The air or the filtered air envelops the object as completely as possible so that an envelope of air is created, which protects the object that is clean from potentially contaminated ambient air as a result of the progressing manufacturing process.

Preferably, the fluid is conditioned air, for example, moistened air, to prevent static loads from building on the object, or to compensate for static loads on the object. Static charging of the objects is avoided through the direct use of the conditioned air at the time of removal of the object from the mold, so that particulates or microbes may be prevented from attaching to the object due to static charges on the object. In a preferred embodiment, the cavity in the container component or part (i.e., resulting from the removal of the core) is aerated immediately with the enveloping gas, in particular the filtered and/or conditioned air, at the time the component or part is removed from the mold.

More preferably, the fluid is deionized air and, most preferably, filtered, conditioned and deionized air. In this way, the object to be handled only comes into contact with the air prepared in this way and, if necessary, a static charge originating at the time of the removal process resulting through the friction may be in statu nascendi, that is to say, immediately compensated for when it occurs. It is also possible, since no more charges are occurring, to no longer do this inside of a plastic matrix, which reacts together with the additional charge effects described below, as they occur in the known procedures.

Furthermore, the envelopment of the object has the effect that the object is in contact with the fluid or the gas or the processed air for a very long time. By comparison with known air showers or air curtains (through which an object or a part of an object is guided for cleaning or through which an object falls due to gravity), the present invention requires relatively low discharge rates and recharging effects, as they occur in the current state of technology, are compensated for or reduced. Preferably the charge of the object may also be measured and the flow of deionized air can be controlled or regulated so that the charge occurring in the object can be precisely compensated for without resulting in a renewed undesired charge. In addition the grippers holding the object may be grounded so that charges are dissipated.

The fluid by which the object is enveloped may also preferably contain, at least as a component, a sterilizing fluid or gas. The sterilization of microbes can also result through the use of a microbicidal fluid or admixtures of germicidal substances to the fluid or the gas. For example a gas containing $H_2O_2$, ozone or something similar, may be used as a sterilizing gas. As an alternative to sterilizing gas, purified air, $CO_2$, noble gases or other gases may be used for enveloping or sheathing the object, in particular at the time of removal from the mold. The present invention contemplates the use of any and all suitable gases that create a substantially pure atmosphere in the immediate environment of the object to prevent contamination by the environmental air.

The envelopment of the object functionally starts when the object is still in the mold. More preferably, the envelopment or the sheathing of the object starts immediately after the mold is opened so that the object manufactured in this way does not contact the environmental or ambient air. In this way, contamination of the sterile or cleanly manufactured object can be securely prevented when the mold is opened and/or the object is removed therefrom, as well as during further processing.

Preferably the removal of the object from the mold is done in a defined way by machine. Through removal by a machine, the object can be removed in a predefined way and at a predetermined speed. By doing so, a desired removal speed is always maintained at which it is guaranteed that the envelope made by the circulating fluid or gas neither drifts away nor is degraded or damaged. Further, the fluid environment or sheathing is preferably maintained during removal (from the mold) and movement of the object. Furthermore, the static charge at the time of removal of the object from the mold can also be minimized through the defined movement. The course and motion of the object's removal with respect to the mold can be controlled in such a way that hardly any particles are formed during removal of the object, for example, due to friction between the mold and the object. The defined removal by machine from the mold may, for example, be done by a robotic arm or by another suitable handling device, which can be operated with predetermined speeds and accelerations.

Most preferably, the object is removed from the mold using a robot and is simultaneously separated or ejected from the mold by an ejector mounted in the mold. This makes it possible to remove an object, especially a plastic object, from the mold while it is still in a relatively soft or semi-molten state. By means of the ejector and the robot that grips the object, the required removal or separation strength is applied to several places on the object to remove the object from the mold. The material of the object only has to support low forces at the time of removal. In this way, isolated acting high forces, which could lead to deformations of an object that is still soft or semi-molten, are avoided.

Preferably the removal of the object from the mold is done with a low starting speed. That means that the object is first detached from the mold with the lowest possible speed. The speed of motion can subsequently be increased a step at a time or progressively increased in order to make fast handling possible. Through the slow start up speed, a clean separation of the object from the surface of the mold can be achieved without any particles remaining attached to the surface of the object due to deformations. Potential contamination of the object during removal from the mold is further minimized in this way.

The removal of the object from the mold is preferably done before total cooling of the object. The removal of the object is done at the highest removal temperature possible, which results in the object or component thereof being in a relatively soft state at the time of removal. The defined removal by machine is also an advantage here since only a machine removal makes a removal without deformities possible when the plastic is still soft compared with an exclusively mold linked deformation of the plastic object.

The plastic that is still soft makes a clean detachment from the surface of the tool possible without the occurrence of undesired particles because the surface of the plastic on a microscopic level exhibits a certain degree of plasticity. Furthermore, static charges due to friction may be minimized. The fluid circulating around the object at the time of removal also operates to cool the object.

The removal of the object from the mold is conducted, in a preferred embodiment, using a robot having at least one nozzle connected to a fluid source for enveloping the object with a fluid. The nozzle or nozzles are preferably arranged as closely as possible on a gripping device of the robotic arm that grips the object. During the removal and motion of the object from the mold by the robot, the object is preferably enveloped or sheathed by the fluid from the ambient air. Preferably, the object is enveloped as thinly as possible to keep the extent of the atmosphere created by the fluid or the gas, and therefore the quantities of fluid, as low as possible, while still providing the benefits of the present invention.

Alternatively or in addition, nozzles may be configured in at least one part of the mold to envelop the object with the fluid. Through these nozzles, the object may already be enveloped in the mold with fluid immediately at the time the mold is opened, so that the object does not contact the ambient air through the entire removal process from the mold. Also, the fluid nozzles may be configured in the moving and/or the stationary part of the mold. The precise configuration depends on the geometry of the mold and on the component to be generated. The nozzles are configured in such a way that, at the time of removal, the object or component is enveloped with fluid or gas, in particular with high purity air, in order to prevent impurities from attaching or adhering to the object.

The mold preferably exhibits a surface, which is treated in such a way that it exhibits a minimal contact power. This also contributes to there being no undesired particles occurring at the time of removal, which could potentially attach to the surface of the object. So from the outset a sufficiently clean object is created which does not require any subsequent cleaning, since in compliance with a preferred embodiment of the invention it is shielded from the ambient air by an enveloping fluid. The surface of the mold is preferably designed with a surface roughness that is neither too small nor too large in order to achieve the least possible bond between the object and the mold. In addition, the surface of the mold may be coated with suitable materials such as Teflon or titanium nitride. All other suitable coatings or procedures for the treatment of mold surfaces may also be used in order to realize a minimum attachment between the object created and the mold.

In addition to the enveloping fluid the object may also be surrounded by a protective bell immediately upon removal from the mold in addition to envelopment with the fluid. One of these types of protective bells is at least a single sided, open hollow part so that the object can get into the bell through the opening. The bell may be made, for example, from plastic or metal and is preferably fixed to a robotic arm, which removes the object from the mold and handles it further. At the same time the fluid flowing around the object, in particular a gas, is preferably conducted in such a way that it completely fills the bell so that no potentially contaminated ambient air gets into the bell. The bell has the advantage that drifting of the fluid or gas layer that is enveloping the object is prevented, even when the movement of the container part by the robotic arm is fast. Thus, the bell of the present invention provides an adequate shield from the environmental air when the object is being moved.

Preferably, an automatic or a semi-automatic subsequent treatment follows at the time of removal of the object from the mold. This may include one or several subsequent processing steps, such as, for example in the case of a medical container or a part of a container, siliconization, inspection, assembly, labeling, filling and packaging steps. These further processing may be done in a closed plant (e.g., in a separate facility or in the same facility in which the molding step was completed) in which sufficient conditions, such as Class 10,000 conditions, prevail, such as is known, for example from U.S. Pat. No. 6,189,292, U.S. Pat. No. 6,263,641, U.S. Pat. No. 6,250,052 and U.S. Pat. No. 6,164,044. A greater freedom is permitted in the subsequent process steps because the objects or parts molded according to a preferred embodiment of the present invention are substantially pure prior to being passed on to further processing, and therefore the overall contaminant load for the objects are barely approached after the molding step. This outcome can be contrasted with current processes, from which the molding step typically contributes a substantial portion of contaminant load for the entire process.

Preferably, however, the shielding of the object removed from the mold by the enveloping fluid is also maintained during one or more of the subsequent handling and/or processing steps. It is also possible to do away with the Class 100 clean room during these subsequent handling and/or processing steps since the object, preferably a part of a container, is protected from the environmental air through the shielding or the envelopment of the object. In order to maintain this fluid envelope, in particular an envelope made out of substantially pure air, corresponding air nozzles are conveyed along with the product or with the container part. Preferably the required nozzles are configured directly on the robotic arm that moves the object. As a result, the object is kept in the protective fluid envelope throughout the entire process, and transfers between different environments through appropriate gates become unnecessary (which results in a less complex, less risky and less costly process).

The envelopment of the object removed from the mold with the fluid may be used to quickly cool off the container part. For example, a targeted fast cooling of the object may be desired in the case of partial crystalline plastics or for the prevention of crystallization. An appropriately fast and defined cooling can be achieved through the appropriate tempering of the fluids with which the object is being enveloped.

Alternatively, the envelopment of the object removed from the mold can be used for a slow cool down. This may be desirable, for example, for the removal or prevention of cooling stresses in amorphic plastics. The fluid used may be appropriately tempered to achieve a targeted slow cooling of the object. Through the appropriate tempering and control of the volume flow of the fluid, the cooling speed of the object removed from the mold can be adjusted across a wide range depending on the type of the plastic or of the material used.

The object is preferably fitted together or assembled with other components, either in the same facility or separate facilities. Both the object as well as the other components, if required, can be protected from contaminants from the environmental air through a fluid environment or sheathing, as described above.

In particular the object may be a container, for example, a medical container, which is to be fitted together with other components and/or filled and closed. Several or all of the components of a container to be fitted together may be removed from a mold and handled in the previously described way. In this way barrels, plungers and/or tip caps of a syringe to be prefilled, for example, may be appropriately handled so that all of the parts of the container or of a prefillable syringe coming in contact with a drug during the entire production or handling process are protected from environmental impurities.

In addition, at least individual procedural steps may take place in a Class 1000, 10,000 or 100,000 controlled environment or at a lower purity. A Class 100 clean room environment, such as is required by the current state of technology, is not necessary in compliance with the invention since the object to be handled or, more precisely, the container part to be handled, is shielded from contaminants by the enveloping fluid. Of course, the more pure clean room classifications (e.g., Class 10 or 100) do not deteriorate the result and may be brought into use in any of those procedural steps where they are required in accordance with regulatory guidelines for example.

In compliance with a further preferred embodiment of the invention, a siliconization of the object takes places immediately following removal of the object from the mold. Such a siliconization is, for example, required for the manufacture of prefillable medical containers. A siliconization step conducted immediately after removal of the object from the mold, when the object is preferably not quite totally cooled down, has the advantage that the surface of the object is already activated. So no additional activation prior to siliconization is required for plastic objects, as a result of which the manufacturing procedure is further simplified and accelerated. Following siliconization, a visual inspection with the naked eye or one done automatically with a camera, can be carried out where the flawless state of the object as well as the quality of the siliconization are able to be checked simultaneously.

Furthermore, the fluid enveloping the object can also be used to influence the surface characteristics of the object. The fluid, and in particular the gas, can be selected in such a way that predetermined reactions with the surface layer of the object are entered into in order to achieve certain surface characteristics. Alternatively, corresponding auxiliary agents can be mixed with the fluid. In addition, auxiliary agents and reactants can be removed again through the fluid flow.

A special preference is to use the fluid enveloping the object to harden and/or dry a surface coating. The surface coating may, for example, be silicon, which is applied during a siliconization step. The enveloping gas, which protects the object from environmental influences, may be used to accelerate the drying or the hardening of the silicon.

The invention also concerns a device for the handling of a substantially pure object, in particular a medical object such as a medical container or part of a container. The handling device includes at least one nozzle for the discharging of a fluid. At the same time the nozzle for the discharging of the fluid is configured in such a way that the fluid envelops an object being held in the handling device. Consequently, at least one nozzle is configured in such a way that the fluid flows over those parts of the object which are to be protected from the environmental air so that the fluid can form a protective layer or a protective envelope around the object. The precise configuration and number of the nozzles used depends on the shape of the object to be protected.

Preferably the handling device is a robotic arm with a gripping device to secure the object. At least one nozzle is configured close to the gripping device. In this way the object can be as directly as possible in the flow so that the casing formed by the fluid flow is placed as closely as possible to the object. In this way the amount of the fluid required is reduced and a closely defined atmosphere surrounding the object is created, for example, from a substantially pure gas.

Furthermore, there is preferably a protective shield configured on the handling device, which at least partially covers the fluid being discharged. Such a protective shield serves to prevent a distortion or a displacement of the fluid when the handling device is moved. Therefore, the protective shield is preferably configured at least in the path of the motion in front of the fluid casing and in front of the object lying in the casing. In a preferred embodiment, the protective shield takes the form of a bell that sheathes not only the object but also the fluid surrounding the object, so that the fluid casing protecting the object can be maintained when the handling device is moved quickly.

The present invention, along with the attributes and attendant advantages thereof, will best be appreciated and understood in view of the following detailed description taken in conjunction with the accompanying drawings.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the text that follows, the invention is described in terms of manufacturing and/or handling a medical container using the enclosed Figures. In these:

FIG. 4 shows a horizontal projection of a first preferred embodiment for enveloping an object, such as a medical syringe, in a protective fluid;

FIG. 5 shows a perspective view of the preferred embodiment shown in FIG. 4;

FIGS. 16A-16E are flowcharts of a manufacturing process performed in conjunction with a preferred embodiment of the present invention;

DETAILED DESCRIPTION OF THE PRESENTLY PREFERRED EMBODIMENTS

The present invention is described below in terms of molding and/or processing a medical syringe. However, it is contemplated that the systems, devices and methods of the present invention can be used, implemented with or incorporated into the molding, manufacture, processing and/or handling of any object that needs to be produced and/or maintained in a pure or substantially pure condition.

Figure 1:
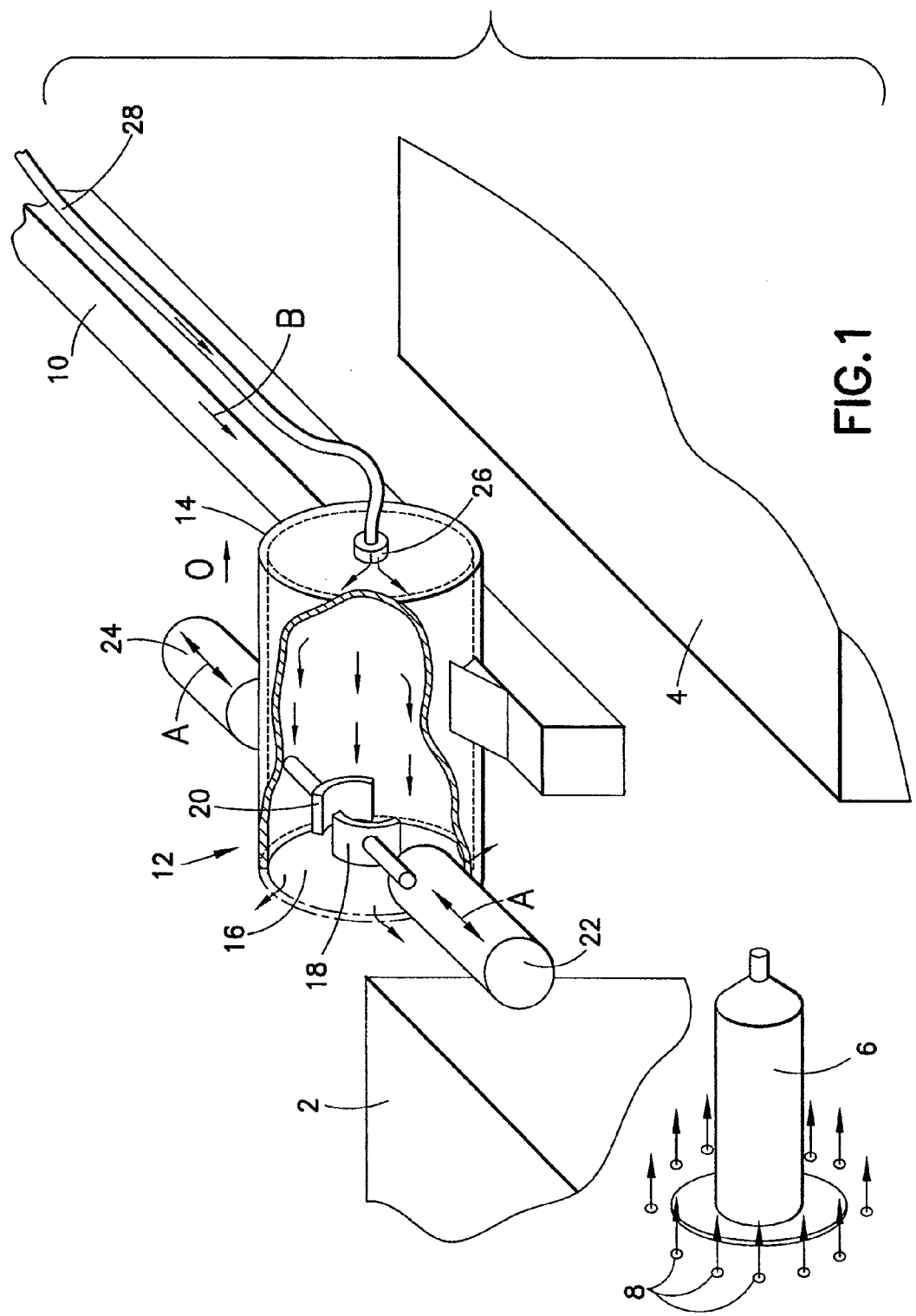
FIG. 1 shows a perspective view of a preferred initial step in a molding operation of the present invention.
Figure 2:
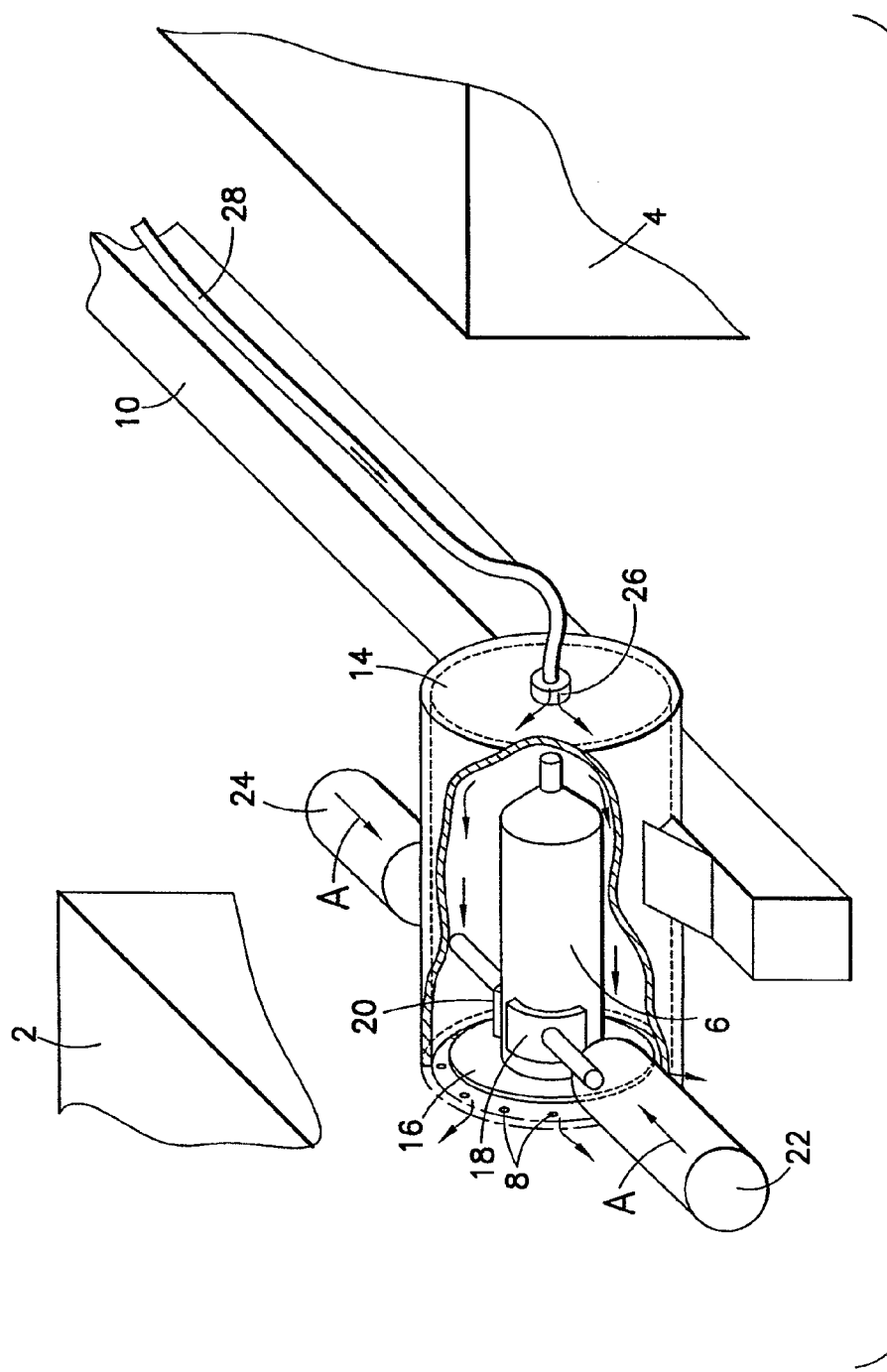
FIG. 2 shows a perspective view of a preferred second step in a molding operation of the present invention.
Figure 3:
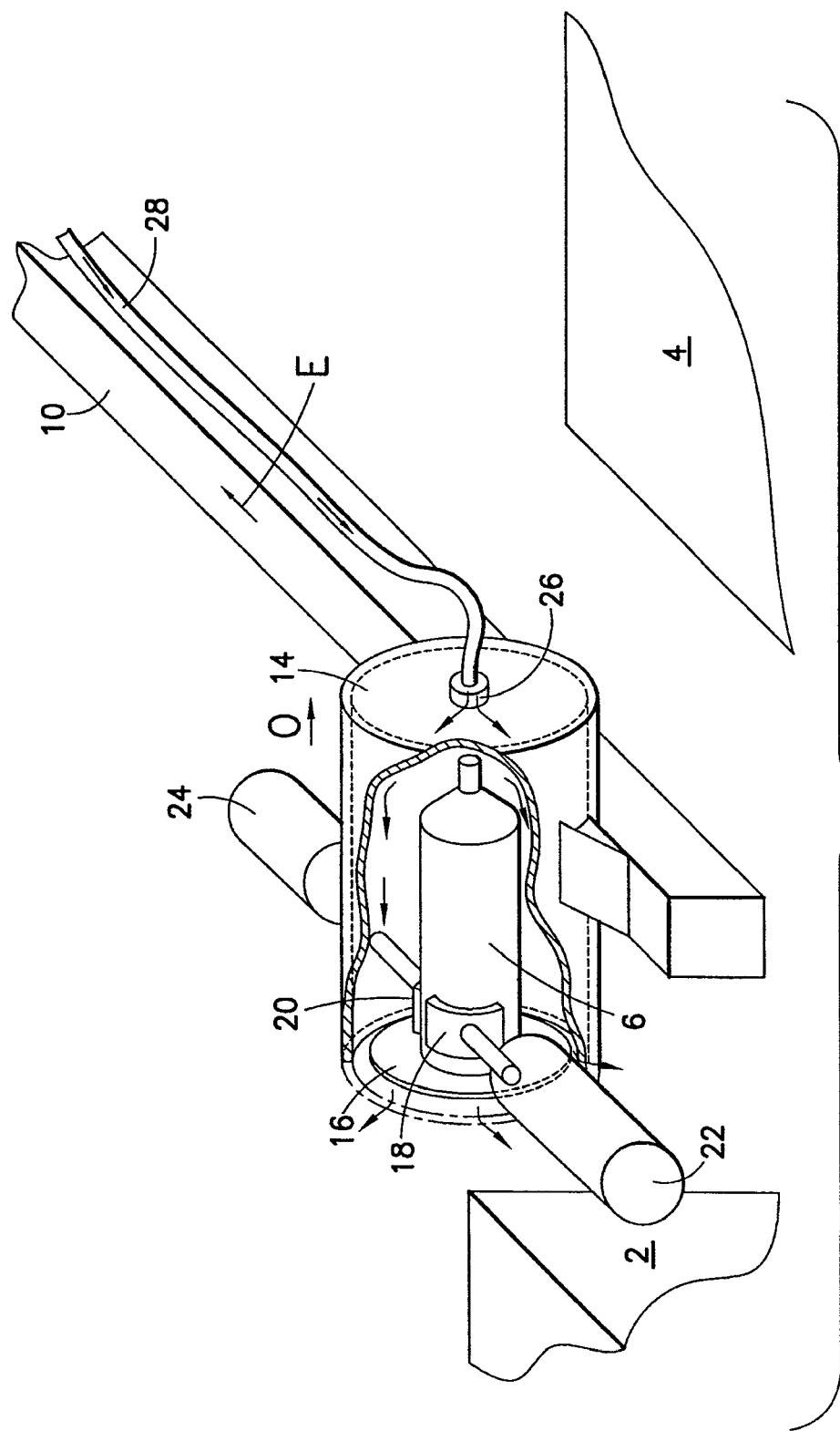
FIG. 3 shows a perspective view of a preferred third step in a molding operation of the present invention.

A preferred embodiment for molding or manufacturing a container part according to one or more preferred aspects of the present invention is described schematically in FIGS. 1-3. FIG. 1 shows an initial procedural step in which both halves of the mold 2 and 4 are opened. The container part made in the mold 2, 4 in the form of a plastic syringe 6 is still on a mandrel on the mold 2. There are jets 8 configured in a ring surrounding the mandrel on the mold 2, through which gas, preferably deionized and conditioned substantially pure air, flows out in the direction of the arrows shown in FIG. 1. The discharge of the air preferably starts with the opening of the mold halves 2 and 4. The direction of the flow goes in such a way that the air flows as linearly as possible along the lengthwise direction on the outside of the syringe 6. In this way the container part, that is to say the syringe 6, is surrounded and protected from contaminants from the environmental air by a protective shell made from substantially pure air, which flows out of the jets 8. Furthermore, this procedure works with deionized air that discharges any static charges in the syringe 6 potentially created when the mold halves 2 and 4 are opened. In this way it is possible to prevent particles from settling down on the surfaces of the syringe as a result of these static charges.

Furthermore a robotic arm 10 is shown in FIG. 1, on which is fixed a gripping device 12 for the removal of the syringe 6 from the mold half 2. The gripping device 12 initially consists of a cylindrical bell 14, which defines an opening 16 on its face, through which the syringe 6 can be taken in. In the area of the foremost end of the bell 14 (i.e., the ends turned towards the opening 16), there are two grippers 18, 20 to hold the syringe 6 configured facing each other. The grippers 18 and 20 are able to be moved using actuating drives 22, 24 lengthwise in the direction of arrow A in order to grip the syringe 6. The actuating drives 22 and 24 may, for example, be actuated hydraulically, pneumatically or electrically. On its rearmost end, the bell 14 exhibits a gas entry opening or a nozzle 26, which is connected with an air supply device. Preferably substantially pure, deionized and conditioned air is conducted through the line 28, the gas entry opening or nozzle 26 in the direction of the arrow in FIG. 1, and into the inside of the bell 14. At the same time, the air flows in parallel to the lengthwise direction of the bell 14 to the opening 16 and exits through this opening into the open air.

To remove the syringe 6 from the mold 2, the robotic arm 10 is first moved in the direction of arrow B until the opening 16 of the bell 14 is positioned opposite the syringe 6. Subsequently the robotic arm 10 is moved in the direction of arrow C so that the bell 14 and the grippers 16 and 18 are pulled over the syringe 6, as is shown in FIG. 2. The bell is moved in the direction of arrow C in FIG. 1 to the point that it completely encloses the syringe 6. At the same time the syringe 6 finds itself between the grippers 18 and 20. The grippers 18 and 20 are moved by the actuating drives 22, 24 in the direction of arrow A in FIG. 2 so that the syringe 6 is squeezed between the grippers 18 and 20. Simultaneously, substantially pure, deionized and conditioned air flows in continually through the gas entry opening 26 in the bell 14 and flows inside of the bell along the outside of the syringe 6 and subsequently exits through the opening 16 on the bell 14 to the open air. When the bell 14 completely surrounds the syringe 6 in the way shown in FIG. 2 the flow of gas through the jet 8 in the mold 2 can be switched off because the syringe 6 in this position is completely enveloped by the gas or the airflow in the bell 14. The air flow in the bell 14 has the effect that the syringe 6 is totally protected from the environmental air and in this way is shielded from contaminants from the environmental air.

After the syringe 6 has been gripped by the grippers 18 and 20, the robotic arm is moved away in the direction of arrow D in FIG. 3. Simultaneously the appropriate mold ejector may, if necessary, support this movement so that the isolated force working on the syringe can remain low. This allows for removal to take place at relatively high temperatures. In individual cases, however, it is possible to do away with the grippers 18, 20 as well as the ejector. At the same time, the syringe 6, which is held in the bell 14 by the grippers 18, 20, is peeled off a mandrel of the mold halves 2. With this movement the airflow in the bell 14 is continued as is shown by the arrow in FIG. 3. This means that the syringe 6 is completely surrounded with substantially pure, deionized air in the inside of the bell and therefore protected from the environmental air. The volume resulting from the pulling out of the syringe is filled with purified and conditioned air so that primarily the inside of the syringe stays clean and a potential charge is neutralized at its origin. Simultaneously, when there is a fast movement of the robotic arm, the bell 14 protects against the air flow drifting and against the protective casing formed by the air flow around the syringe 6 being distorted. In this way the syringe 6 can be reliably protected from contaminants when it is being moved or removed from the mold 2, 4.

In connection with the movement in the direction of arrow D, the robotic arm 10 executes a movement in the direction of arrow E in FIG. 3, through which the syringe 6 is taken out of the space between the mold halves 2 and 4. Further, the syringe 6 may be conveyed by the robotic arm 10 to further processing steps where the syringe is, for example, siliconized, inspected, assembled, filled, packaged, etc. Also during these further processing steps, the syringe preferably remains in the robotic arm and/or the syringe 6 is, preferably by the appropriate nozzles, surrounded with substantially pure air in order to prevent contaminants from contacting the syringe.

The preceding description is based simply on a preferred embodiment and methodology of the present invention. The invention may be embodied and conducted in many different ways. So, for example, the bell 14 on the robotic arm can be done away with. At the same time, the grippers 18, 20 as well as the actuating drives 22, 24 may be configured directly on the robotic arm 10. There are corresponding air nozzles on the robotic arm 10, which are configured in such a way that one of the grippers 18, 20 holding the component part, for example a syringe, can be completely surrounded with gas without the bell 14 in order for it to be protected from contaminants.

Using FIGS. 4 and 5, an initial arrangement is shown for the envelopment of a substantially pure object, such as a syringe 6. Even if the example is based on the handling of a syringe 6, other substantially pure components can certainly also be handled in the same way. A horizontal projection is to be seen in FIG. 4 and a perspective view of the arrangement is to be seen in FIG. 5. The arrangement consists of two pipes 30 which each exhibits a large number of nozzles 32. In the example shown the pipes 30 extend in parallel to one another and in parallel with the longitudinal axis of the syringe 6. A row of nozzles 32 is arranged over the entire length of the pipes, through which a fluid or a gas is discharged in order to enclose the syringe 6 and by doing so to protect it from the environment. On one end the pipes 30 are connected with a system of pipelines 34 through which the fluid, in particular a gas, for example substantially pure air, is lead into the pipes 30. The flow of fluid is indicated by arrows in FIGS. 4 and 5. At the same time, the nozzles 32 are arranged in such a way that the flow is directed at the syringe 6 from two sides fundamentally in a 90° angle to one another so that the syringe can be completely enveloped by the fluid from all sides and the syringe 6 is shielded by the fluid and protected from the environmental air.

Figure 7:
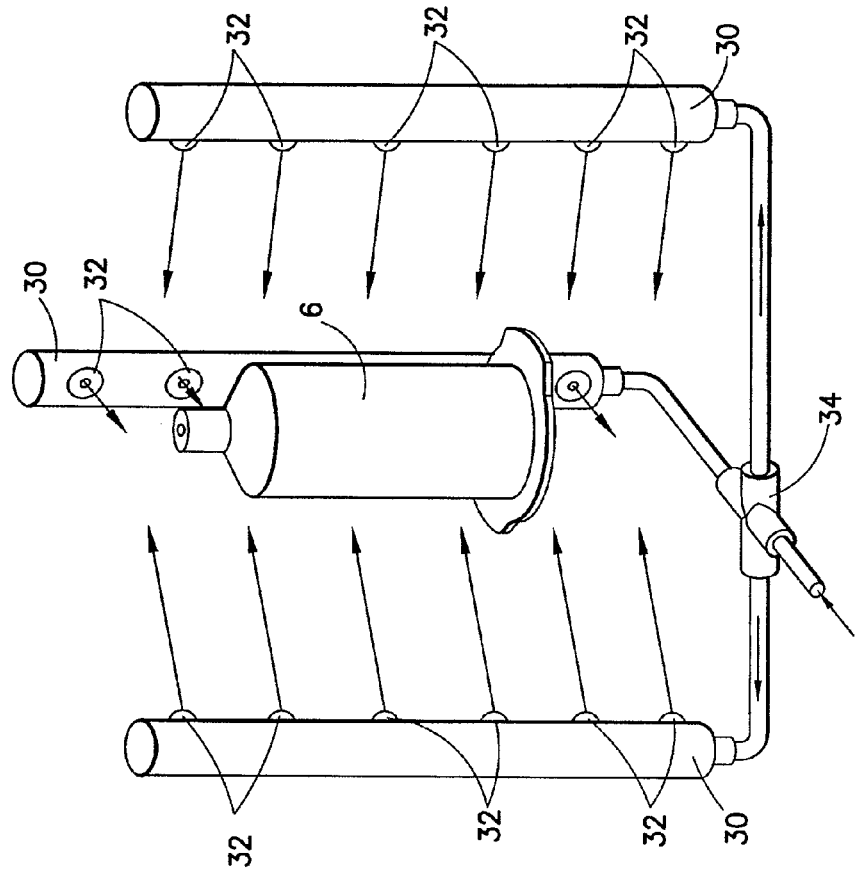
FIG. 7 shows a perspective view of the further preferred embodiment shown in FIG. 6.
Figure 6:
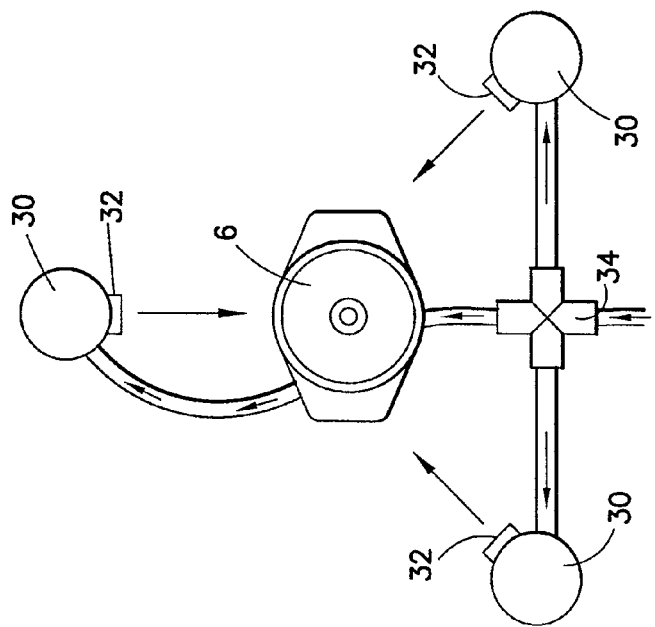
FIG. 6 shows a horizontal projection of a further preferred embodiment for enveloping an object in a protective fluid.

FIGS. 6 and 7 show a variation of the arrangement shown in FIGS. 4 and 5. By contrast to the arrangement shown in FIGS. 4 and 5, there are three pipes provided in the arrangement, which pipes simultaneously distribute fluid around the perimeter of the syringe 6 to be protected so that the syringe 6 is enveloped with fluid from all sides, as is indicated by arrows in FIGS. 6 and 7. In other respects, the arrangement of the pipes 30 corresponds with the arrangement described in FIGS. 4 and 5. The three pipes 30 are connected with a piping system 34 to supply the fluid or the gas, where the flow of the fluid in the piping system is shown in FIGS. 6 and 7 using arrows.

Figure 9:
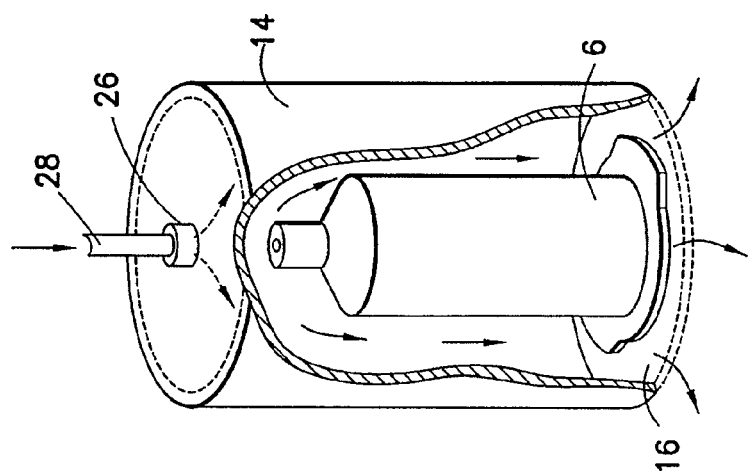
FIG. 9 shows a partially cropped perspective view of the preferred embodiment shown in FIG. 8.
Figure 8:
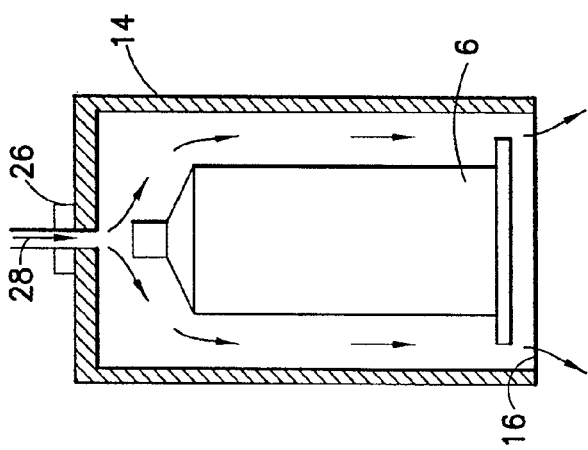
FIG. 8 shows a sectional view and a horizontal projection of yet another preferred embodiment for enveloping an object in a protective fluid.

FIGS. 8 and 9 show a further arrangement for the envelopment of a substantially pure object, such as a syringe 6, with a fluid, for example, a gas such as substantially pure air. In FIGS. 8 and 9, the syringe 6 is surrounded by a bell 14. FIG. 8 shows a horizontal projection and a sectional view of this arrangement, while FIG. 9 shows a partially cropped perspective view. The bell is formed cylindrically and has an opening 16 on one side through which the syringe 6 may be inserted into the bell 14 or the bell 14 may be pulled over the syringe 6. The bell 14 is closed on the opposite back side and exhibits a gas entry opening or a nozzle 26, which is connected with piping 28 for the feeding of a fluid or of a gas. The fluid flows into the bell 14 through the nozzle 26 as is indicated by the arrows in FIGS. 8 and 9. At the same time the fluid flows over the outside of the syringe 6 so that the fluid forms a protective casing. Subsequently the fluid exits the bell 14 through the opening 16. In this arrangement the bell serves the purpose of preventing a drifting of the enveloping fluid when the syringe 6 is moved. In this way it can be guaranteed that the protective casing made from the enveloping fluid can be maintained even when there is rapid motion.

Figure 11:
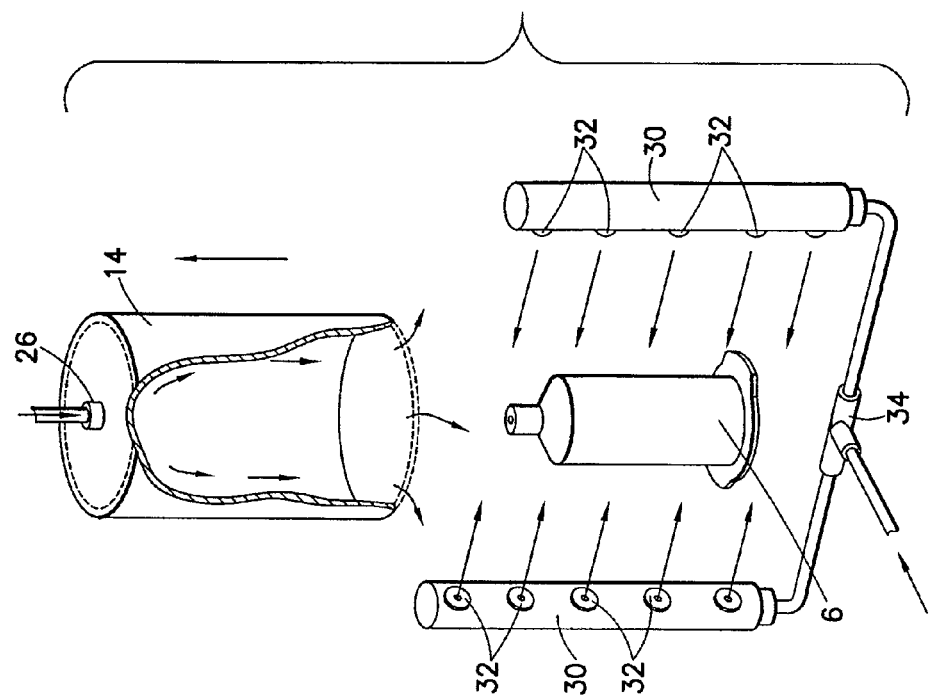
FIG. 11 shows a perspective view of the preferred embodiment shown in FIG. 10.
Figure 10:
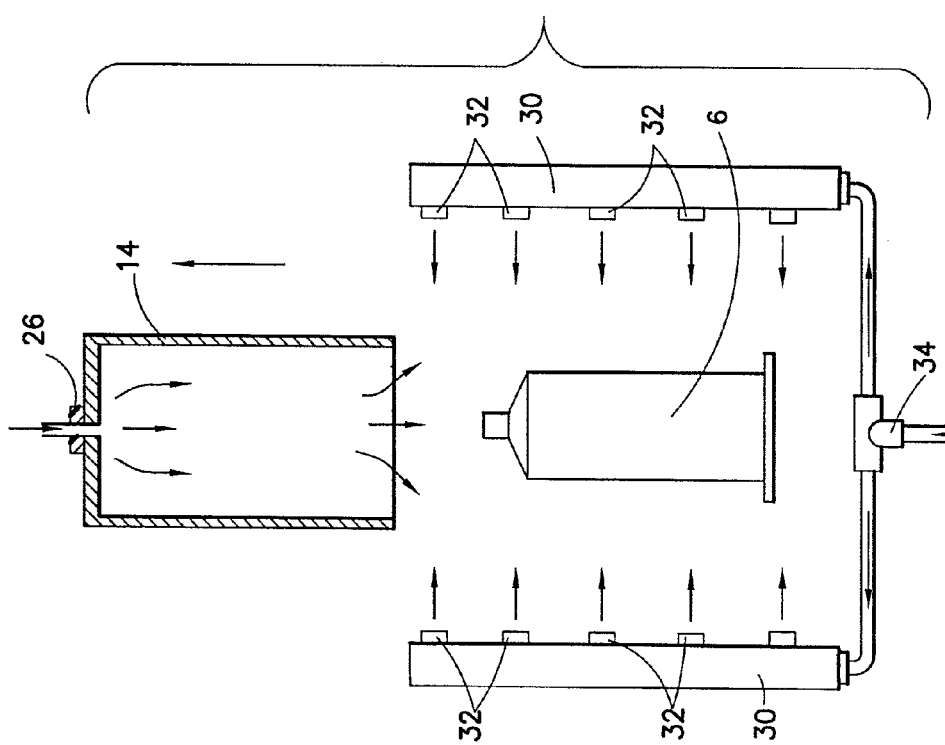
FIG. 10 shows an elevational view, partially in cross-section, of still another preferred embodiment for enveloping an object in a protective fluid.

FIGS. 10 and 11 illustrate how an object, such as s syringe 6, can be transferred out of a bell 14 and into the fluid environment shown in FIGS. 4-7. In addition, FIG. 10 shows a partially cropped side view and FIG. 11 shows a partially cropped perspective view. First of all the bell 14 with the syringe 6 arranged in it (see FIGS. 8 and 9) is put in position between the pipes 30. In FIGS. 10 and 11 an arrangement with two pipes 30 is shown. An arrangement with fewer or more pipes, for example, three pipes as explained using FIGS. 6 and 7 might also be provided for. Subsequently the bell 14 is raised, as a result of which the syringe remains between the pipes 30. At the same time the protective fluid flows out of the pipes 30 through their nozzles 32, just as out of the gas entry nozzle 26 in the bell 14, so that the syringe 6 is completely enveloped by the fluid even when the bell 14 is being lifted. When the bell 14 is removed, the syringe 6 is freely accessible for further processing steps, for example, labeling or inspection or assembly as well as all the work on the outside surfaces. At the same time, however, a protective casing is maintained around the syringe 6 by the fluid discharging from the nozzles 32 of the pipes so that a contamination of the syringe 6 from the environmental air can be prevented. The flow of fluid is also indicated with arrows in FIGS. 10 and 11.

Figure 13:
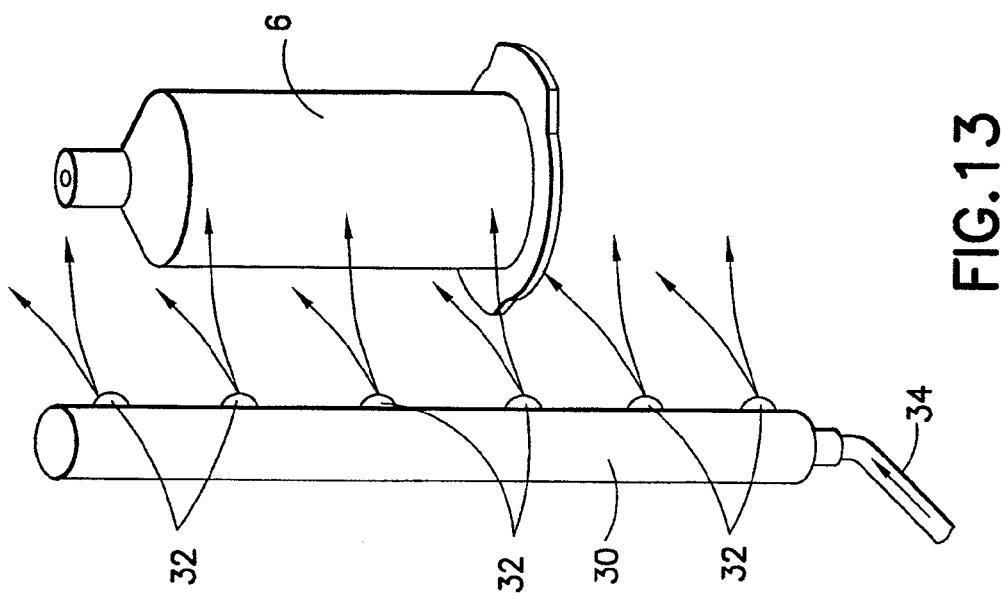
FIG. 13 shows a perspective view of the alternate embodiment shown in FIG. 12.
Figure 12:
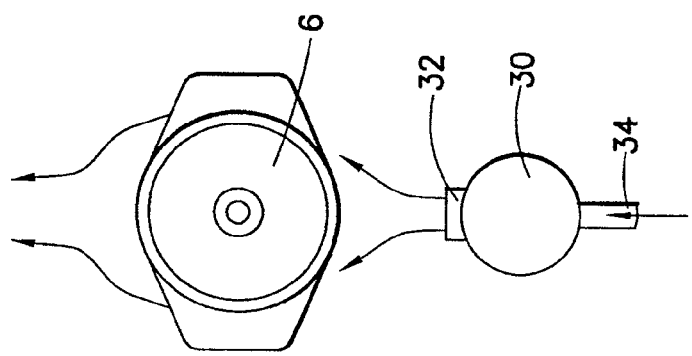
FIG. 12 shows a horizontal projection of an alternate embodiment for enveloping an object in a protective fluid.

FIGS. 12 and 13 show an arrangement similar to the FIGS. 4 through 7 in which, however, only a single pipe 30 is planned for. The pipe 30 extends substantially parallel along the longitudinal axis of the syringe 6 so that the nozzles 32 are turned towards the syringe 6. At the same time the discharging fluid envelops, as is shown in the horizontal projection shown in FIG. 12, the syringe 6 in such a way that the flow on the back side of the syringe 6, that is to say on the side of the syringe 6 turned away from the pipe 30, merges so that a closed liquid casing is formed which protectively encloses the syringe 6 from all sides. Such an arrangement is primarily suited to an object such as a syringe 6 with a round profile, which makes it possible for the liquid to merge. Different types and different numbers of nozzles 32 or pipes 30 have to be arranged around the perimeter of the object depending on the shape and the size of the object to be protected in order to be able to generate a totally enveloping fluid casing around an object.

Figure 14:
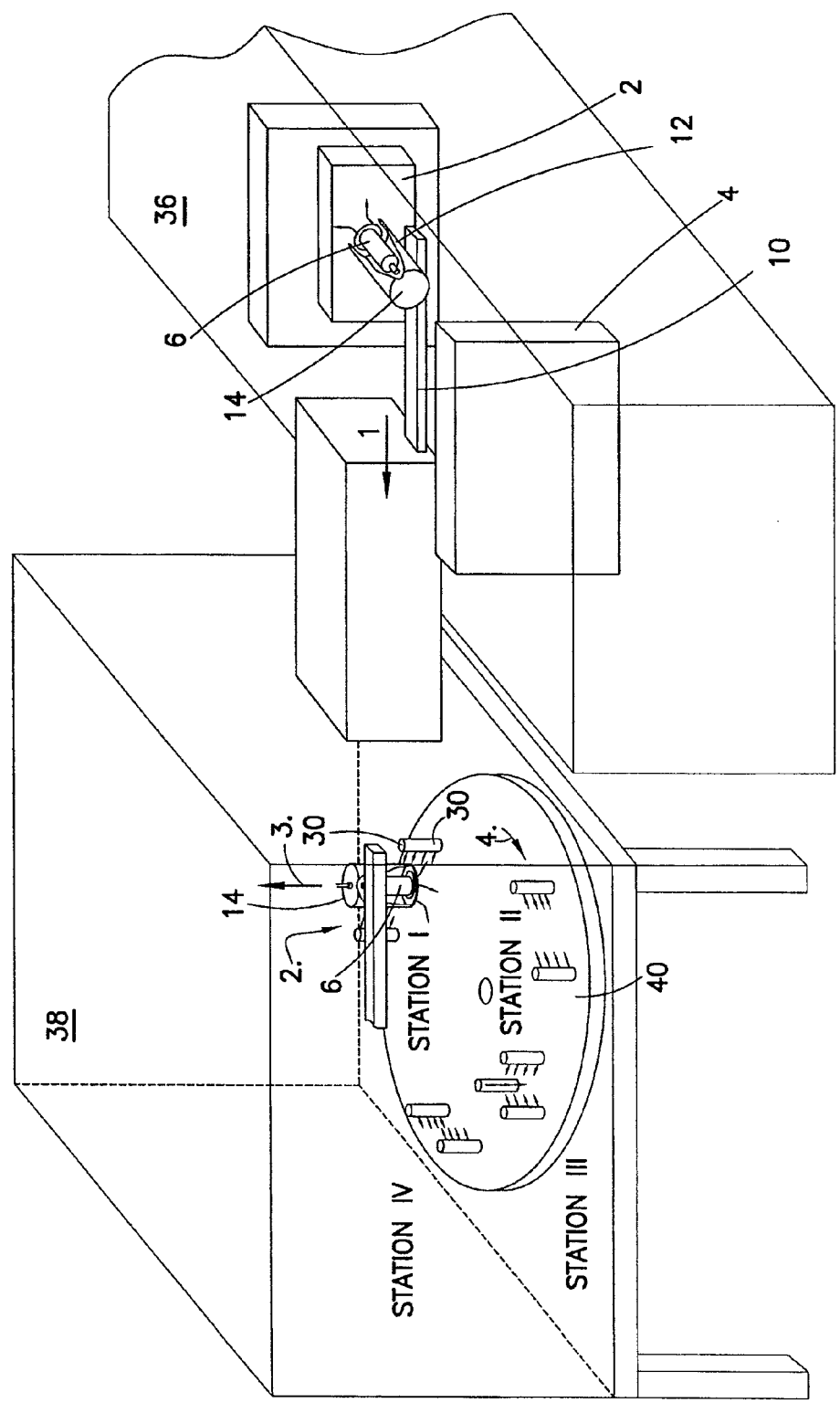
FIG. 14 shows a perspective view of a preferred embodiment of the present invention for manufacturing and processing a substantially pure object.

FIG. 14 shows a schematic, overall view of an arrangement for the production and processing of a substantially pure object. The example shown concerns an arrangement for the production of a medical container such as a syringe 6. The arrangement fundamentally consists of an injection molding machine 36 and a further processing unit 38. The injection molding machine 36 exhibits two mold halves 2, 4 from out of which the syringe 6, as is explained using FIGS. 1-3, is removed using a robotic arm 10 with a gripping device 12 and a bell 14. At the same time a fluid, preferably a gas, constantly flows around the syringe 6 in order to protect the syringe from impurities from the environmental air. Subsequently, the syringe 6 in the bell 14 is transferred by the robotic arm 10 to the further processing unit 38 under the constant envelopment by the gas, as is shown by the arrow in FIG. 14. The further processing unit 38 may be a closed system in which defined environmental conditions prevail.

At station 1 in the further processing unit 38, the syringe 6 from the bell 14 is transferred into an arrangement in compliance with FIGS. 4 through 7 or FIGS. 12 and 13, as is explained in more detail using FIGS. 8 and 9. The arrangement of the pipes and a holder for the syringe are configured on a carousel 40, which forwards the syringe together with the pipes 30 to stations II, III and IV by turning in the direction of the arrow 4. The number of the required stations depends on the processing steps during the further processing. Other configurations of pipes 30 are shown at stations II, III and IV. This should indicate that different arrangements of pipes 30, for example in compliance with FIGS. 4-7 and 12-13, can be configured on the carousel 40 depending on the application purpose and the type of the object.

The further processing steps for the syringe 6 may include, for example, siliconization, inspection, assembly (i.e., with other syringe or container parts or components) and/or filling of the syringe 6. To do this the syringe 6 is forwarded from station to station at which each processing step is performed, by the turning of the carousel 40. At the same time the pipes 30 turn towards the syringe 6 with the carousel 40, so that a fluid constantly envelops the syringe 6. In this way a protective fluid casing can be maintained throughout the entire further processing, which protects the syringe 6 from contaminants from the environment.

Figure 15:
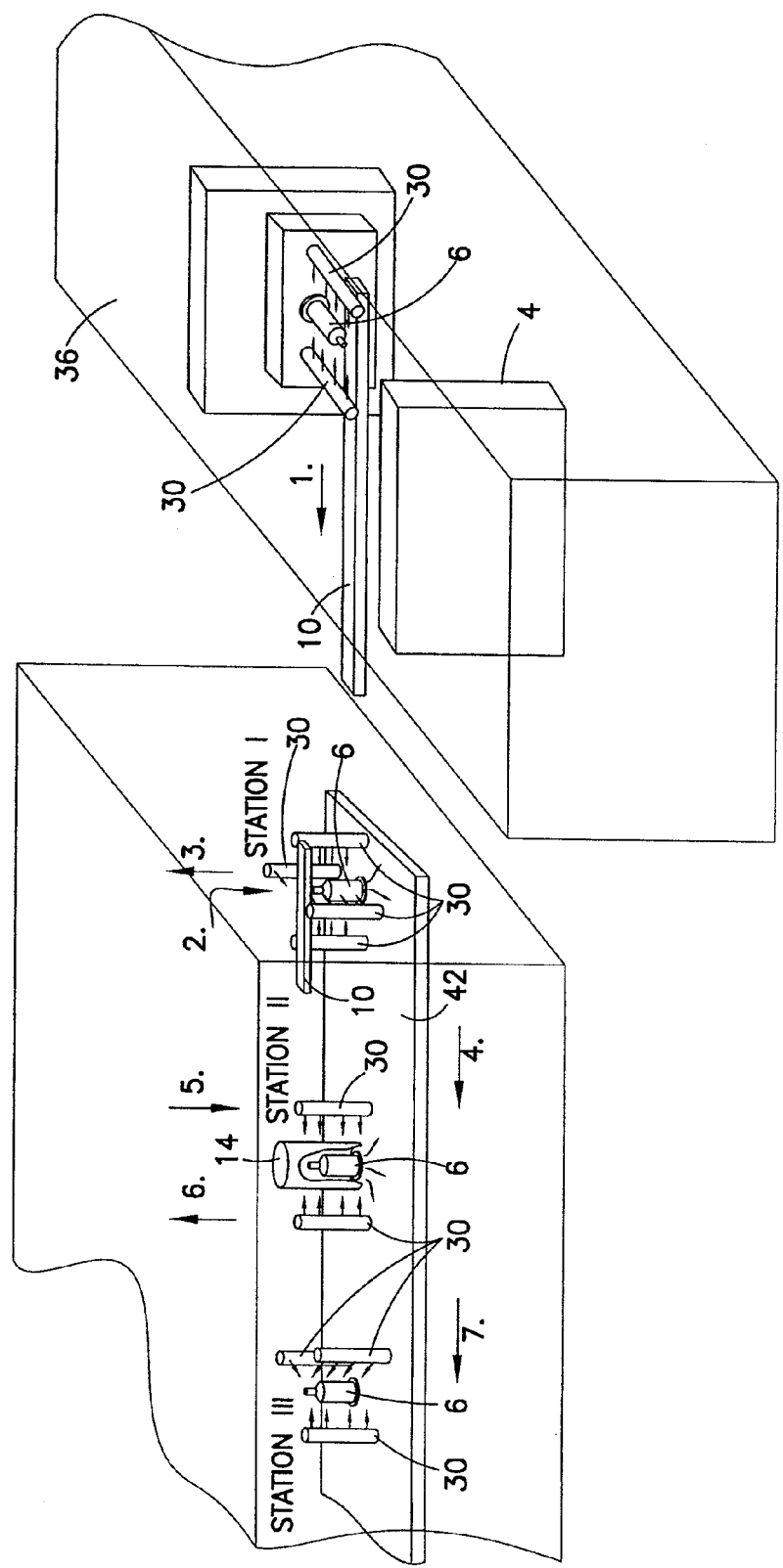
FIG. 15 shows a perspective view of an alternate embodiment of the present invention for manufacturing and processing a substantially pure object.

FIG. 15 shows an alternative arrangement to FIG. 14. The arrangement shown in FIG. 15 is similar to that shown in FIG. 14. The injection molding machine 36 corresponds with the injection molding machine described in FIG. 14. By contrast to the arrangement shown in FIG. 14, there is no bell 14 configured on the robotic arm 10. Instead of the bell 14, there are two pipes 30 with nozzles 32 configured on the robotic arm through which the fluid is conducted around the syringe 6, in order to form a protective casing. Other than for that difference, the set up of the gripping device 12 is as explained in FIGS. 1-3. The syringe 6 is removed from the injection molding machine 36 in compliance with the above description and transferred to the further processing unit 38. In contrast to the arrangement shown in FIG. 14, there is no carousel 40 in the further processing unit 38. Instead there is a linear table 42 configured to transfer the syringe 6 together with the surrounding pipes 30 from station I to station II to station III, etc., depending on how many processing stations are provided. Different processing steps are performed at the processing stations, including, for example, siliconization, inspections, assemblies, etc. The syringe 6 is preferably moved between the stations together with the surrounding pipes 30, and the pipes 30 are configured on the linear table 42 so that the protecting fluid casing is constantly maintained.

First of all the syringe 6 is deposited at station I by the robotic arm 10 between the pipes 30 on the linear table 42. This transfer is done in a similar way to the transfer explained using FIGS. 8 and 9, with the difference that, instead of a bell 14, pipes 30 are configured on the robotic arm 10. At the same time, the pipes 30 on the robotic arm 10 move between the pipes 30 on the linear table 32, so that the fluid can constantly envelope the syringe 6. In the place of the pipes 30 on the robotic arm 10, a bell 14 may also be provided in this arrangement, as is indicated at station II. At the same time the transfer between the pipes 30, as explained using FIGS. 8 and 9, would be done. Furthermore, various numbers of pipes 30 could be configured at the respective uptake positions for a syringe 6, as is shown through the various arrangements at station I, station II and station II. The numbers of the pipes depends on the geometry of the syringe 6 or of an object that is to be protected, and on the processing step to be executed. The arrangement is always selected in such a way that the object or the syringe 6 can be adequately protected from impurities by the surrounding fluid. In the example shown in FIGS. 14 and 15, different arrangements of pipes 30 at the individual stations are shown for the representation of different forms of execution. However, the syringe 6 is forwarded from station to station in the same arrangement of pipes 30 by the carousel 40 or by the linear table 42, as is indicated by arrow 4 and arrow 7.

FIGS. 16A-16E show a preferred embodiment of a manufacturing and assembly process for a medical syringe, according to the teachings of the present invention. The process may include a number of separate manufacturing processes that merge during various assembly steps. For example, a number of syringe components, including one or more of the barrel, plunger substrate, plunger cover and tip cap, may be molded or otherwise formed in a single facility of separate facilities. Likewise, the various components may be assembled to form a syringe in a single facility or may be separately packaged and sent to a separate facility for assembly and/or filing with a fluid, such as a drug or other pharmaceutical.

In the preferred embodiment, as shown in FIGS. 16A-16E, the syringe barrel and plunger substrate are molded in a common facility and the plunger cover and tip cap are molded or otherwise formed in separate facilities and are shipped to the common facility where the barrel and plunger substrate are molded for assembly. Also, carriers (not shown) that are used to hold the molded syringe barrels during subsequent shipment may be molded at the same facility (such as in another room) or at a separate facility and then shipped to the common facility for use.

Figure 16A:
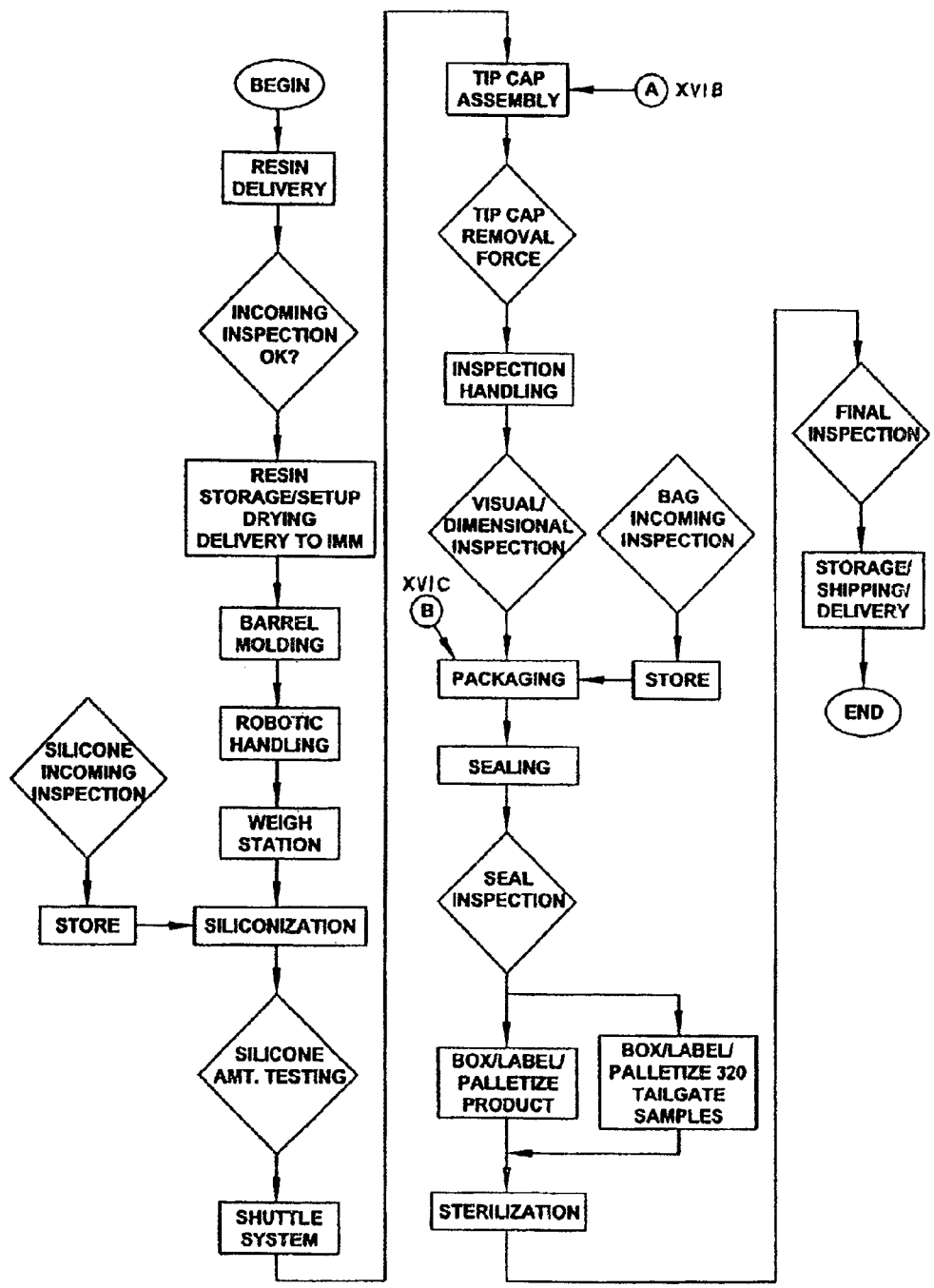
Figure 16B:
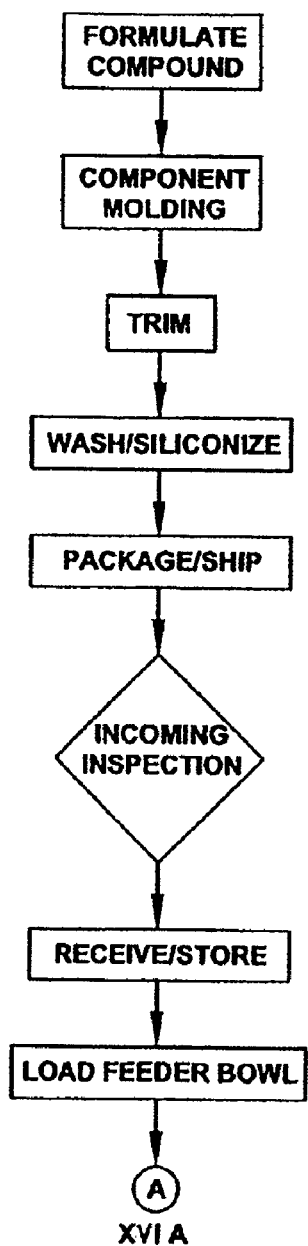
Figure 16C:
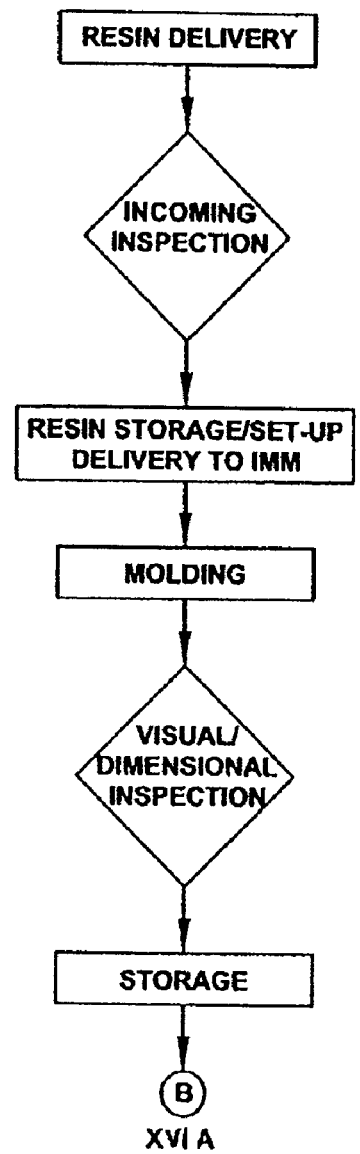

As shown in FIGS. 16A-16C, according to the preferred embodiment the syringe barrel is molded, weighed, siliconized, assembled with a tip cap (shipped from a separate facility), inspected, packaged in a carrier, inserted in a bag, sealed, boxed, sterilized, inspected and then shipped to another facility for subsequent filling with a fluid.

Figure 16E:
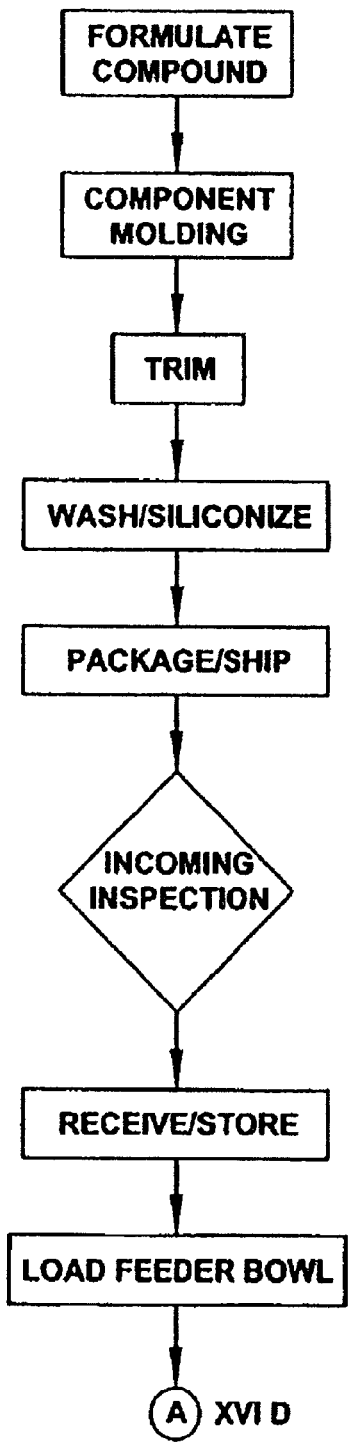

Further, as shown in FIGS. 16D-16E, the plunger substrate is molded, inspected, assembled, siliconized, assembled with a plunger cover (shipped from a separate facility), packaged, sealed, boxed, sterilized, inspected and then shipped to the same facility as the syringe barrel and tip cap assembly for subsequent placement within the syringe barrel to complete the final syringe assembly.

Figure 17:
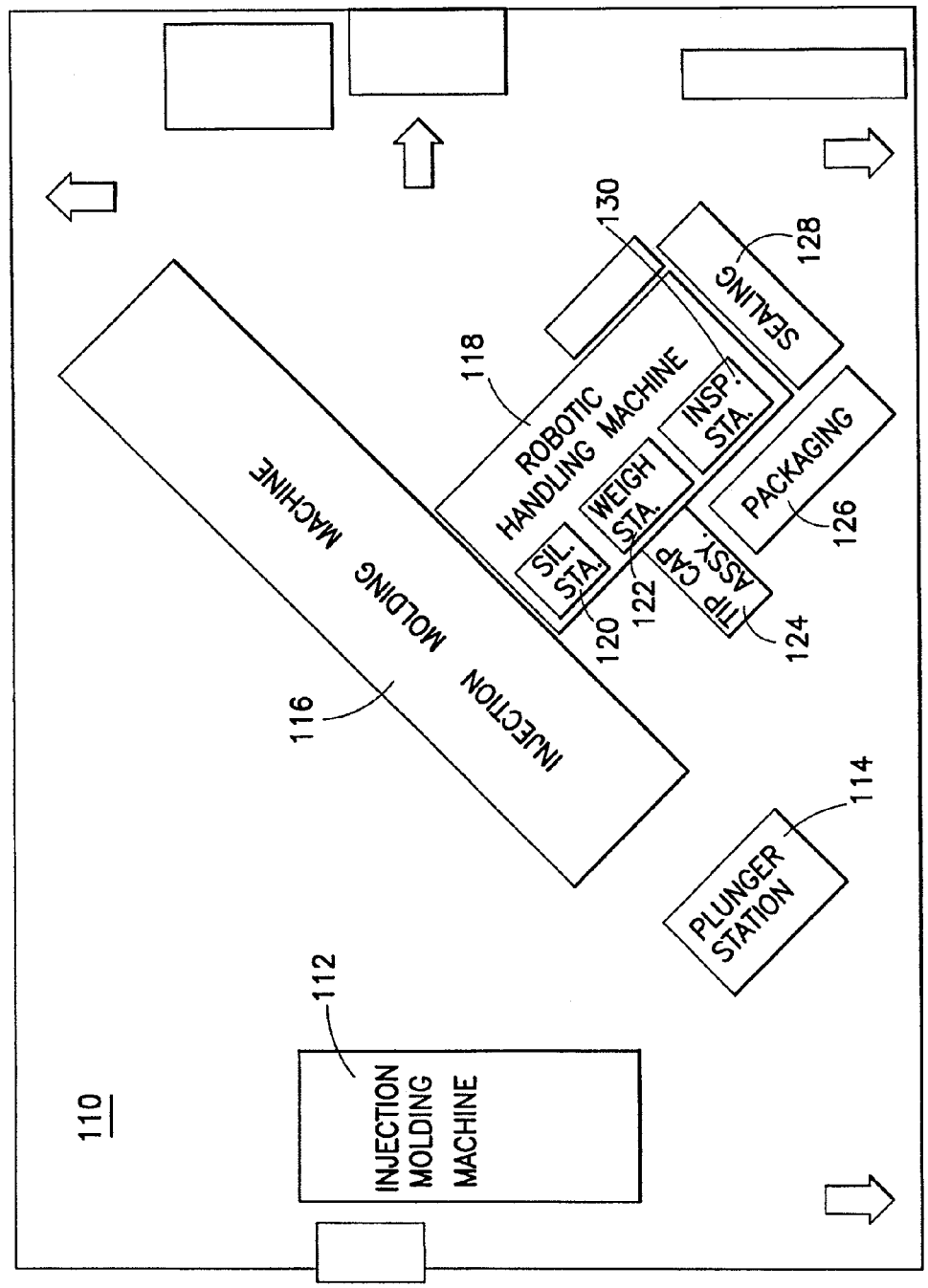
FIG. 17 is a diagram showing the layout of a manufacturing line used in conjunction with a preferred embodiment of the present invention.
Figure 18:
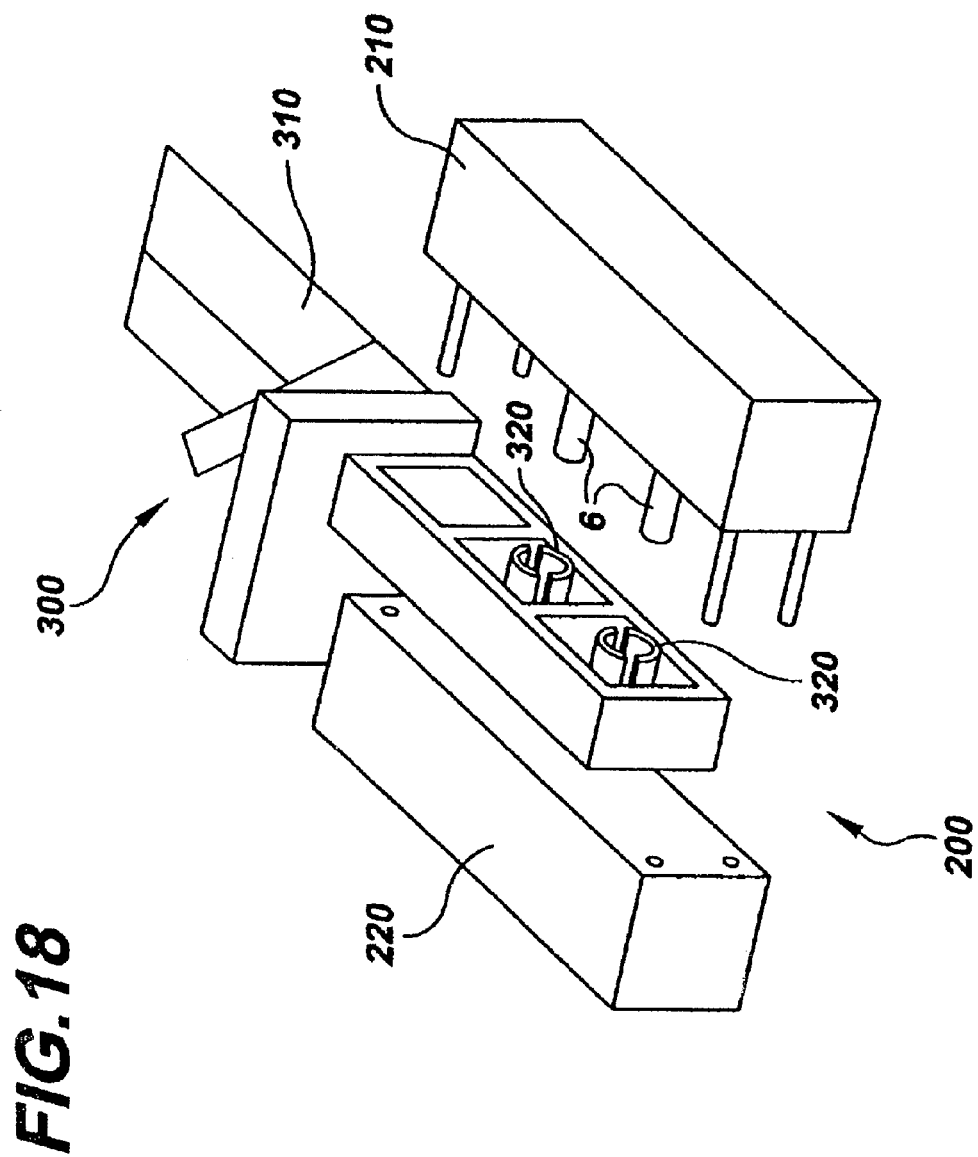
FIG. 18 is a perspective view of a preferred embodiment of a mold and a robotic machine of the present invention.

A facility or room layout for the process shown in FIGS. 16A-16E is depicted in FIG. 17. In a preferred embodiment, the room or facility 110 is a Class 100,000 clean room. The room includes an injection molding machine 112 for plunger components and a station 114 for plunger siliconization, plunger substrate and plunger cover assembly, and packaging of the assembled plunger.

In addition, the room 110 includes an injection molding machine 116 for the syringe barrel and a robotic handling machine 118 (described in detail above) for removing the molded syringe barrel from the molding machine 116. The room also preferably includes a weighing station 122 and a siliconization station 120 for the syringe barrel. After siliconization, the syringe barrel is transferred to a tip cap assembly station 124, where tip caps (preferably provided from a separate facility) are assembled to the syringe barrels to seal the discharge ends or outlets thereof. Before or after tip cap assembly, the barrels may be inspected at station 130, by visual or camera inspection, to confirm the quality of the product After tip cap assembly, the assembled barrels are transferred to a packaging station 126 where the barrels are placed on carriers, and the barrels and carriers are placed in bags. The bags are then delivered to a sealing station 128, where the bags are sealed.

FIGS. 18-21 illustrate a preferred embodiment of the mold and robotic handling machine of the present invention. The mold 200 preferably includes a movable platen 210 and a stationary or fixed platen 220 and the robotic handling machine 300 preferably includes a robotic arm 310 having a pair of handling devices or grippers 320 for gripping and removing the molded syringe barrels 6 from the mold 200. In alternate embodiments, the mold 200 may be adapted to mold one, three or more articles and the robotic handling machine 300 may be adapted to include a corresponding number of handling devices 320.

Figure 19:
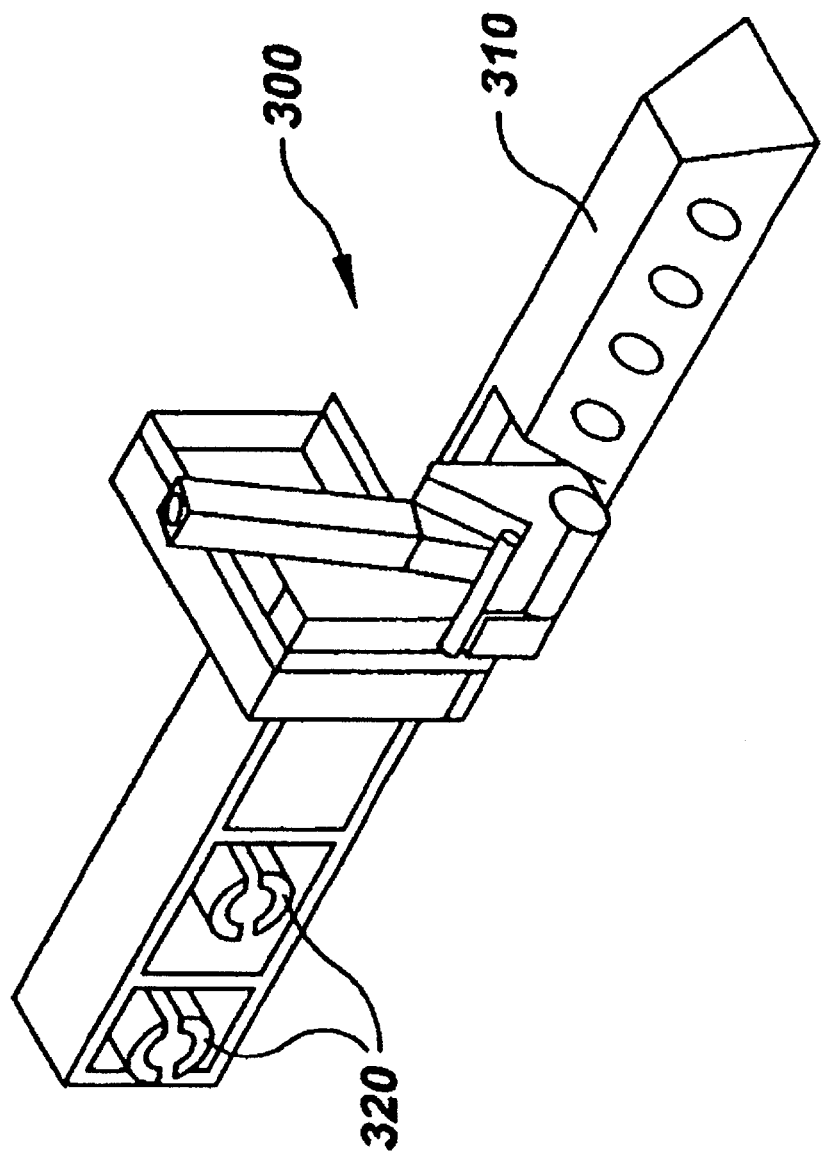
FIG. 19 is a perspective view of the preferred embodiment of the robotic arm and handling device shown in FIG. 18.
Figure 20:
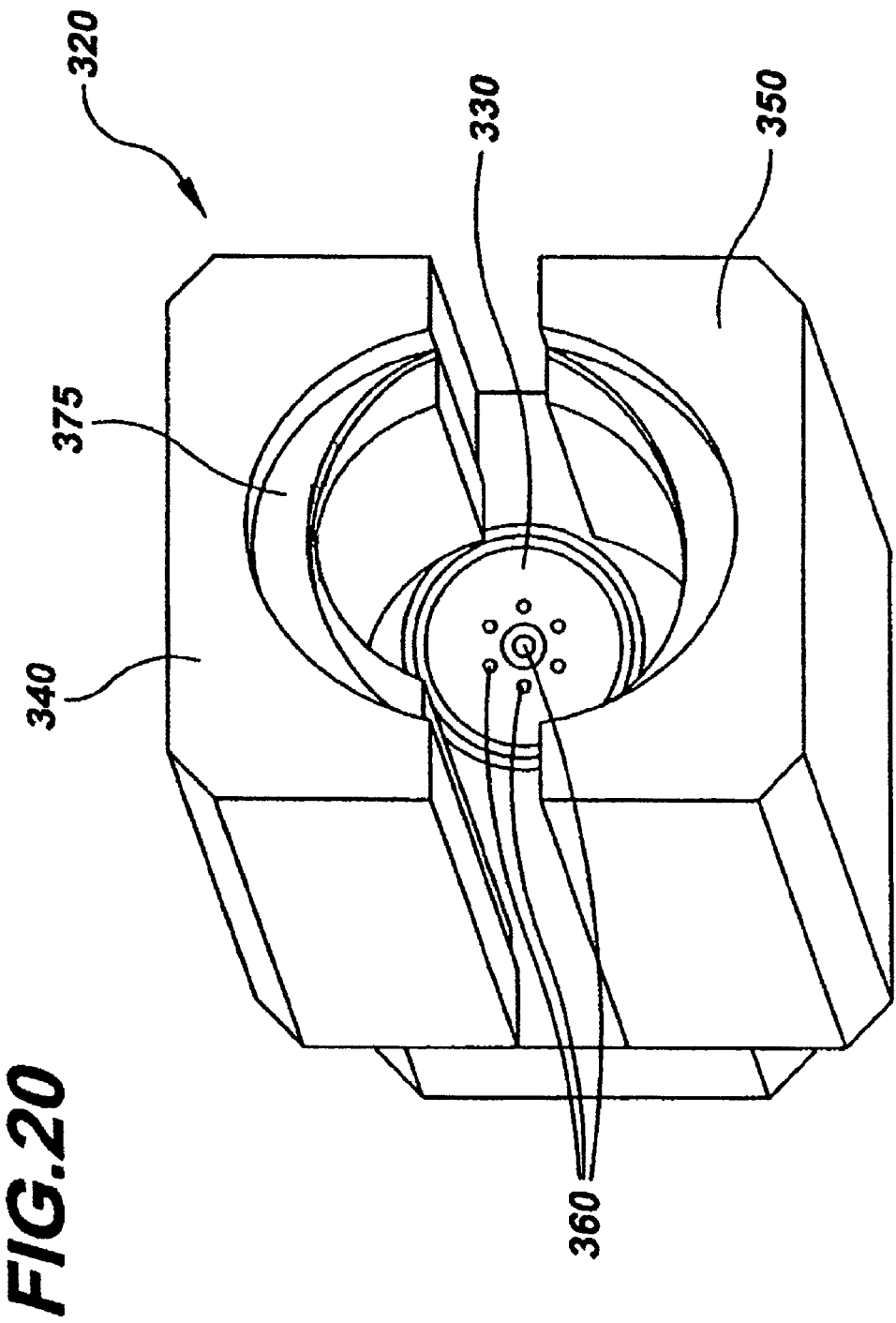
FIG. 20 is an enlarged, perspective view of the handling device shown in FIGS. 18 and 19.
Figure 21:
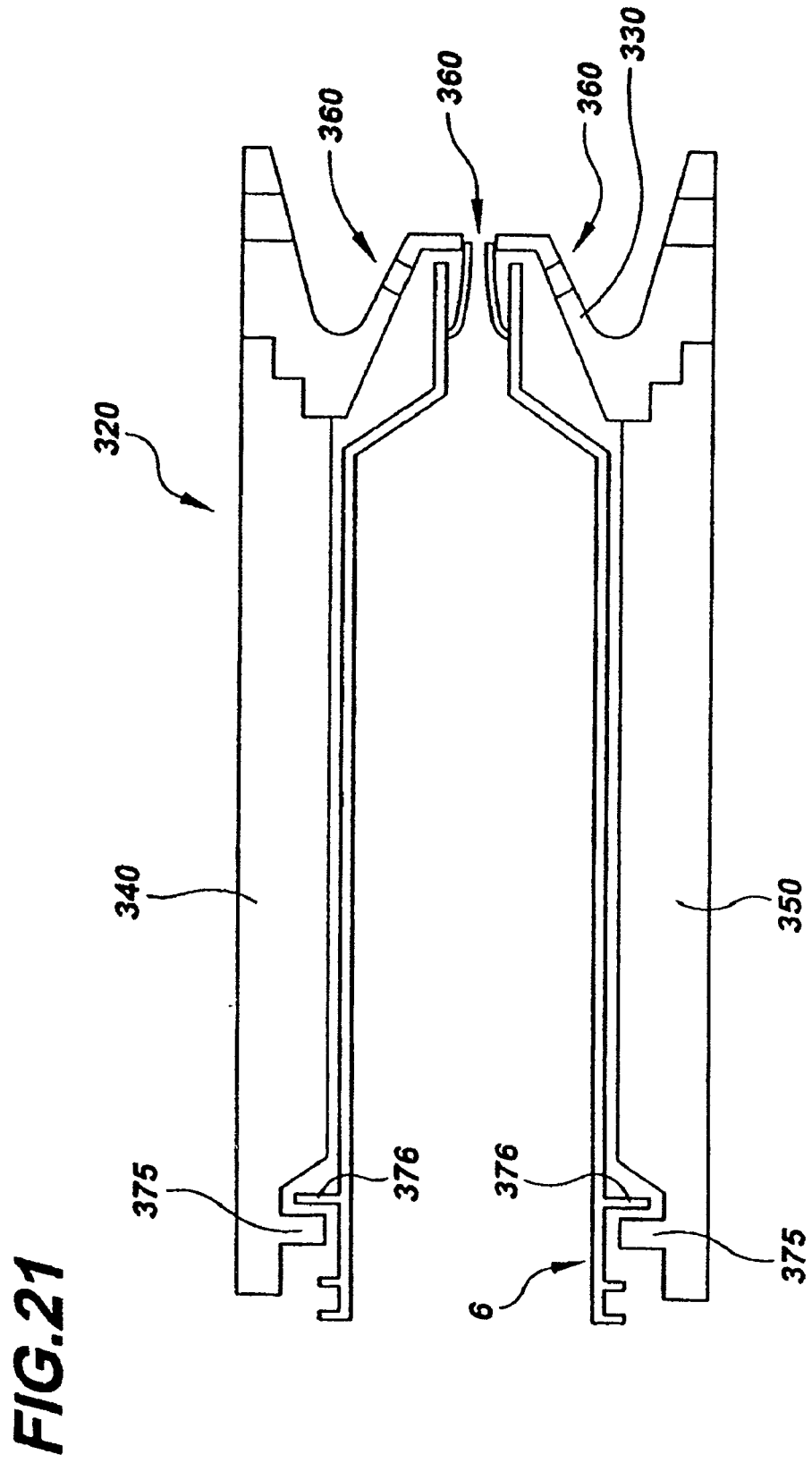
FIG. 21 is a cross-sectional view of the handling device shown in FIGS. 18-20, with a syringe barrel being held therewithin.

As best shown in FIGS. 19-21, each handling device or gripper 320 preferably includes a partially cone-shaped back plate 330, an upper semi-cylindrical member 340 and a lower semi-cylindrical member 350. Preferably, each of the upper member 340 and the lower member 350 defines a shoulder or flange 375 adapted to engage a circumferential flange 376 formed on the syringe barrel 6 to retain the barrel 6 within the handling device 320. The back plate 330, the upper member 340 and the lower member 350 are preferably adapted to form a bell-shaped housing that substantially conforms to the shape of the syringe barrel 6, as best shown in FIG. 21. In alternate embodiments, the handling devices 320 can be configured to substantially conform to the shape of the article, part, component or object that is being molded.

In a preferred embodiment of the handling device 320, the back plate 330 includes a plurality of nozzles or inlets 360 for delivering a fluid, such as deionized air, to substantially envelope the syringe barrel 6 during removal thereof from the mold 200 and during one or more subsequent processing steps. Also, the alignment of the syringe discharge outlet 106 with one of the inlets 360 allows the fluid to enter the interior of the syringe barrel to prevent contaminants from attaching or adhering thereto. The nozzles or inlets 360 are connected to a source of fluid, which preferably includes a filter for filtering the fluid. In alternate embodiments, the upper member 340 and the lower member 350 may also include one or more inlets 360 for delivering fluid to substantially envelope the barrel 6.

In a preferred embodiment, as the platens 210, 220 separate, the robotic arm 310 moves linearly between the platens 210, 220 and the movable platen 210 moves the barrels 6 into position to be gripped by the handling devices 320. In an alternate embodiment, the robotic arm 310 may be translated with respect to the movable platen 210 to position the handling devices 320 to grip the barrels 6.

When the barrels are in position, one or both of the upper member 340 and the lower member 350 of the handling devices 320 move into position to grip and retain the respective barrel 6 (by, for example, the syringe flange 376) therewithin. As a barrel 6 is gripped, an ejector (not shown) on the mold 200 may be used to facilitate removal of the barrel from a core pin (not shown) thereof. Once the barrels are retained by the handling devices 320, the robotic arm 310 is linearly removed from between the platens 210, 220 to move the barrels to a subsequent processing step and to permit the mold platens 210, 220 to close to form another set of syringe barrels.

The following devices and/or machines may be suitable for use in the present invention: the molding machine may be a Netstal 1500 injection molding machine provided by Netstal-Maschinen AG of Switzerland; the robotic handling machine may be provided by Hekuma GmbH of Germany; the bag sealing machine may be provided by Kopp Verpackungssysteme of Germany; and the resin dryer may be provided by Mann-Hummel ProTec GmbH of Germany.

Figure 22:
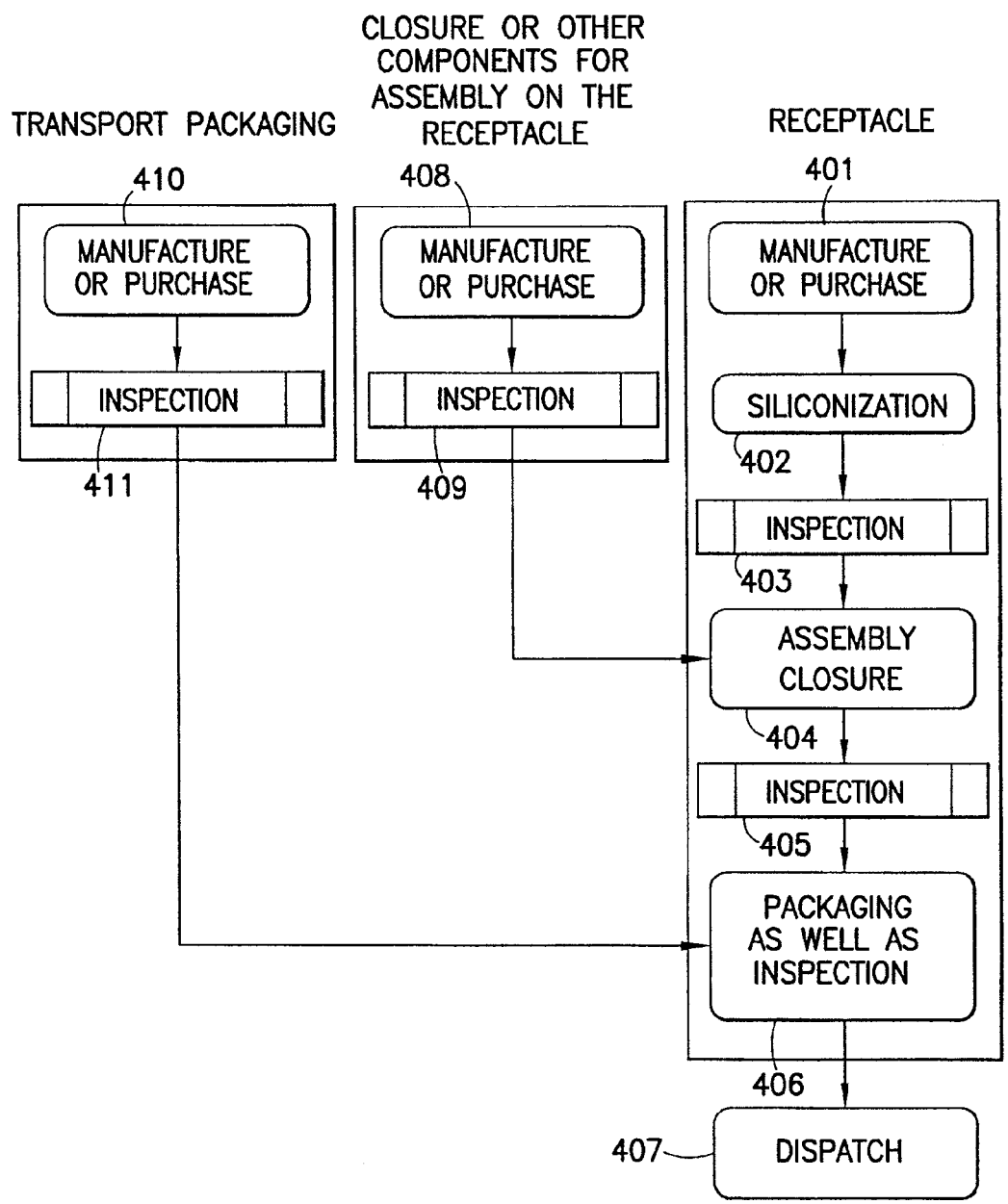
FIGS. 22 and 23 are flow diagrams in which the course of the manufacture of a syringe and/or a medical receptacle according to FIGS. 1 to 15 is shown.
Figure 23:
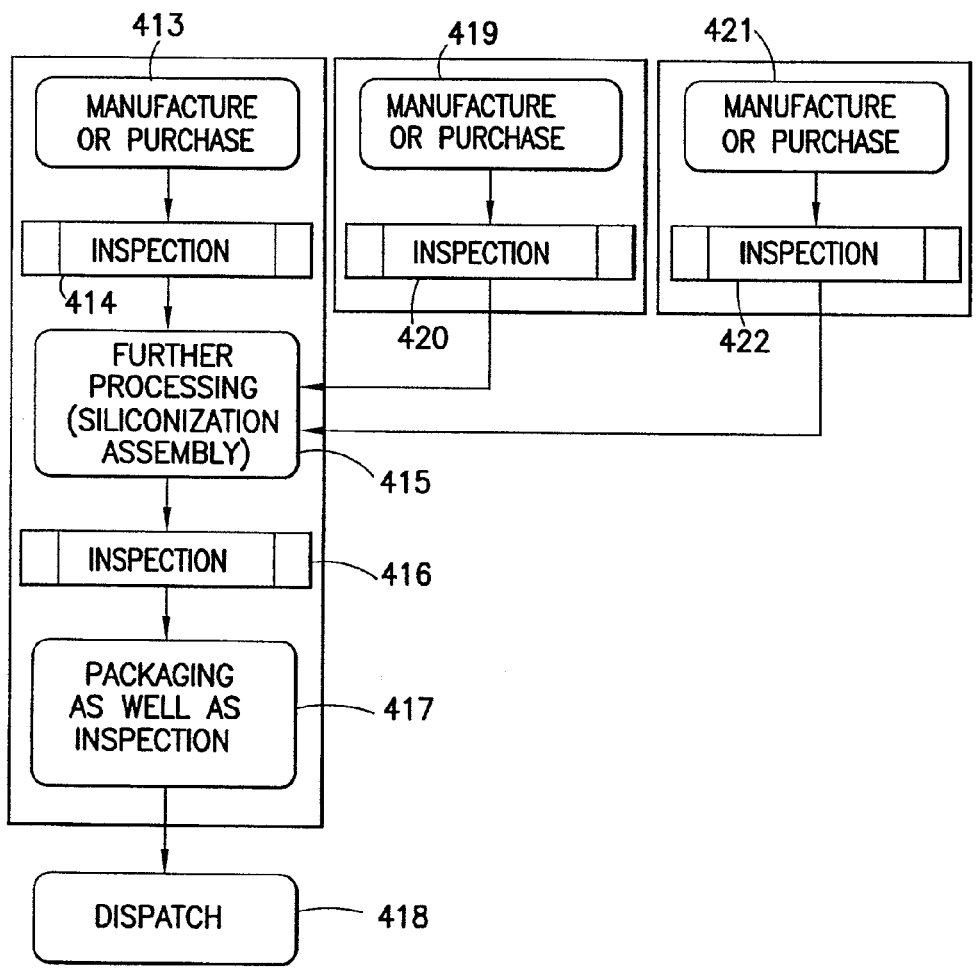

FIGS. 22 and 23 show a preferred embodiment of a manufacturing and assembly process for a medical syringe, according to the teachings of the present invention. The process may include a number of separate manufacturing processes that merge during various assembly steps. For example, a number of syringe components, including one or more of the barrel, plunger substrate, plunger cover and tip cap, may be molded or otherwise formed in a single facility of separate facilities. Likewise, the various components may be assembled to form a syringe in a single facility or may be separately packaged and sent to a separate facility for assembly and/or filing with a fluid, such as a drug or other pharmaceutical.

FIG. 22 id flow diagrams showing the course of the above-described method. With this, not only is the manufacture of the object or the syringe 6 but also the manufacture and assembly of all accessories as well as the packaging described in the flow diagrams. The method steps 401 to 407 in FIG. 22 relate directly to the manufacture of the syringe or/and of the receptacle. In the method step 401, the receptacle or the syringe is manufactured with the injection molding method. With this, as a result of the high temperatures which prevail with the molding, one produces a germ-free, highly pure object. With the removal from the tool, the object or the receptacle, depending on the type of plastic used, preferably has a temperature between 5° C. and 150° C. (PP/PE for example 15° C. to 100° C., PC for example 70° C. to 140° C., PET for example 5° C. to 60° C., PVC for example 20° C. to 85° C. and COP for example 50° C. to 150° C.). A siliconization of the injection molded receptacle is then effected in method step 402. An inspection or control follows this in method step 403. A closure which has been manufactured in the methods steps 408 and 409 as will be described later is then assembled on the receptacle in method step 404. Once again an inspection or control follows this in method step 405, before a primary and secondary packaging with a subsequent inspection once again is then effected in method step 406. The transport packaging is manufactured according to the method steps 410 and 411 to be described later, and are supplied in the method step 406. The dispatch of the finished and packaged product then follows as a method step 407. The method steps 401 to 406 which are surrounded in FIG. 22 by a dotted line all take place under the above described shielding of the object or the receptacle or syringe by way of the highly pure enveloping air. With regard to this, it is the case of a local air flow which flows in a direct manner around the receptacle to be processed and handled. The air is preferably supplied at a pressure between 300 and 3500 hPa. At the same time the air is filtered before leading to the object to be enveloped. The filter applied for this preferably has a pore size between 0.1 and 3 μm and a separation rate significantly above 99%.

The closure which is assembled on the receptacle or syringe in the method step 404 is manufactured in method step 408, likewise with the injection molding method, or is introduced into the process as a purchased part. At the same time the closure is delivered in a highly pure form, or, as described previously with the example of the receptacle, is removed directly from the injection molding machine in a highly pure form. An inspection or testing of the part follows in method step 409 before the closure is assembled on the receptacle in step 404. The transport packaging in which the receptacle is packaged in method step 6 is supplied to the process in method step 410. At the same time the packaging is either supplied as a purchased part in a highly pure, i.e. germ-free or low-germ form, or is removed directly from an injection molding machine as described above by way of the receptacle. The method steps 410 and 411 as well as 408 and 409 are also effected in each case in a manner such that the respective object is shielded from the surrounding air by highly pure air which flows directly around the object, in order to protect it from contamination. This is indicated in FIG. 22 by the dotted lines, i.e. the method steps represented in the dotted lines are carried out whilst using the shielding according to the invention, as has been described in detail above.

FIG. 23 shows a further flow diagram in which the manufacture of a closure and/or other component is shown, which are assembled after filling the receptacle which has been manufactured according to the procedure in FIG. 22. This closure for example is applied into the receptacle or the syringe after the filling and later serves as a plunger on use of the syringe. Corresponding parts of the closure are introduced into the process in the steps 413, 419 and 421. This may either be in the form of purchased parts which are supplied in a highly pure form and fed (sluiced) into the process. Alternatively the parts, as described previously with the example of the receptacle, may be removed thermoformed and in the condition in which the machine is still warm. In this condition the objects are highly pure on account of the high processing temperatures, so that they may be processed further in a direct manner. An inspection or control of the individual parts which are manufactured or supplied in this manner follows in the steps 414, 420 and 422. At the same time the handling of the individual parts in each case takes place amid shielding by way of the highly pure air flowing around the objects, as has been described previously with the example of the receptacle or the syringe. An assembly of the individual parts is effected in method step 415, wherein the components supplied in the method steps 413, 419 and 421 are led together in this method step. Apart from the assembly, one may also effect a siliconization of the components, in particular of the closure serving as a plunger. Subsequently a further inspection follows in step 416, before the object or closure assembled in this manner is then packaged in step 417 and inspected once again. The dispatch of this part is then effected in step 418, which is preferably effected together with the dispatch of the receptacle according to method step 407 in FIG. 22. The method steps in which the handling of a highly pure object is effected according to the method described previously with the example of the receptacle or syringe, are also bordered by dotted lines in FIG. 23.

The foregoing description and accompanying drawings set forth the preferred embodiments of the invention at the present time. Various modifications, additions and alternative designs will, of course, become apparent to those skilled in the art in light of the foregoing teachings without departing from the spirit and scope of the disclosed invention. The scope of the invention is indicated by the following claims rather than by the foregoing description. All changes to the present invention that fall within the meaning and range of equivalency of the claims are to be embraced within their scope.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A device for handling a substantially pure object during manufacture of the object, comprising:
    a handling unit having a gripping device configured to grip and remove the object from a mold in which the object is formed; and
    at least one nozzle arranged proximate to the gripping device and through which one of pure air and gas which is substantially free from microbes or particles is delivered, the at least one nozzle being configured such that the pure air or gas flows over those parts of the object which are to be protected from the environmental air and to envelope the object in an envelope created by the one of the pure air or the pure gas upon opening the mold;
    wherein the at least one nozzle is conveyable with the object by the handling unit to maintain the envelope of the one of the pure air and the pure gas about the object during removal of the object from the mold.

2. The device of claim 1 wherein the handling unit forms a housing for substantially surrounding the object.

3. The device of claim 2 wherein the housing is substantially bell shaped.

4. The device of claim 1 wherein the at least one nozzle comprises a plurality of nozzles.

5. The device of claim 1, further comprising a source of fluid connected to the at least one nozzle.

6. The device of claim 5, further comprising a filter associated with the fluid source.

7. The device of claim 1 further comprising a robotic arm, the handling unit being positioned on the robotic arm.

8. The device of claim 1 further comprising the mold for forming the object.

9. The device of claim 8 wherein the mold comprises a movable platen and a stationary platen.

10. A device for handling a substantially pure object during manufacture of the object, comprising:
    a housing having an open end and a substantially closed end;
    a handling unit having a gripping device configured to grip and remove the object from a mold in which the object is formed connected to the housing;
    at least one nozzle spaced apart from the handling unit and through which one of pure air and gas which is substantially free from microbes or particles is delivered, the at least one nozzle being configured to envelope the object in an envelope created by the one of the pure air or the pure gas upon opening the mold; and
    an air supply device configured to provide the one of the pure air and the gas which is substantially free from microbes or particles
    wherein the at least one nozzle is conveyable with the object by the handling unit to maintain the envelope of the one of the pure air and the pure gas about the object during removal of the object from the mold.

11. The device of claim 10, wherein the housing is substantially bell shaped.

12. The device of claim 10, wherein the grippers are moveable with respect to the object to hold the object and are configured to move one of parallel or perpendicular to a direction of the pure air and the pure gas.

* * * * *